(12) United States Patent
Sugamata

(10) Patent No.: US 10,729,683 B2
(45) Date of Patent: *Aug. 4, 2020

(54) ANTITUMOR AGENT

(71) Applicant: TOCHIGI INSTITUTE OF CLINICAL PATHOLOGY, Shimotsuga-gun, Tochigi (JP)

(72) Inventor: Masao Sugamata, Shimotsuga-gun (JP)

(73) Assignee: TOCHIGI INSTITUTE OF CLINICAL PATHOLOGY, Shimotsuga-Gun (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/183,352

(22) Filed: Nov. 7, 2018

(65) Prior Publication Data

US 2019/0070163 A1    Mar. 7, 2019

Related U.S. Application Data

(63) Continuation of application No. 15/680,493, filed on Aug. 18, 2017, now Pat. No. 10,149,846, which is a continuation of application No. 14/786,089, filed as application No. PCT/JP2014/061264 on Apr. 22, 2014, now Pat. No. 9,775,836.

(30) Foreign Application Priority Data

Apr. 22, 2013 (JP) ................. 2013-089356

(51) Int. Cl.
| | |
|---|---|
| *A61K 31/47* | (2006.01) |
| *A61K 31/381* | (2006.01) |
| *A61K 31/404* | (2006.01) |
| *A61K 31/41* | (2006.01) |
| *A61K 45/06* | (2006.01) |
| *G01N 33/50* | (2006.01) |

(52) U.S. Cl.
CPC ............ *A61K 31/47* (2013.01); *A61K 31/381* (2013.01); *A61K 31/404* (2013.01); *A61K 31/41* (2013.01); *A61K 45/06* (2013.01); *G01N 33/5011* (2013.01)

(58) Field of Classification Search
CPC .................................................... A61K 31/47
USPC ......................................................... 514/311
See application file for complete search history.

(56) References Cited

U.S. PATENT DOCUMENTS 9,775,836 B2    10/2017    Sugamata

FOREIGN PATENT DOCUMENTS

| JP | 2003-532675 A | 11/2003 |
|---|---|---|
| JP | 2005-519095 A | 6/2005 |
| JP | 2007-514002 A | 5/2007 |
| WO | WO 01/85166 A1 | 11/2001 |
| WO | WO 03/074036 A1 | 9/2003 |
| WO | WO 2005/011595 A2 | 2/2005 |
| WO | WO 2006/019874 A1 | 2/2006 |
| WO | WO 2008/105803 A1 | 9/2008 |
| WO | WO 2010/115593 A2 | 10/2010 |

OTHER PUBLICATIONS

Tan, Chinese Journal of Clinical Research 2010, 23, 10.*
Gunning Cancer Research, 62, 4199-4201, 2002.*
Magnusson Cancer Res 2007; 67: (19). Oct. 1, 2007.*
Wang et al. Nat Rev Cancer. 2010, 10(3): 181-193 and Nozaki. Keio J Med 59 (1): Mar. 10-18, 2010.*
Extended European Search Report for European Application No. 14789109.7, dated Nov. 15, 2016.
Geun-Young Kim et al., "Role of the Low-Affinity Leukotriene B4 Receptor BLT2 in VEGF-Induced Angiogenesis," Arterioscler Thromb Vasc Biol., vol. 29, No. 6, pp. 915-920, 2009.
Gunning et al., Cancer Research, vol. 62, pp. 4199-4201, Aug. 1, 2002.
Hirotoshi Akita, "Molecular Biology of Lung Cancer", Japanese Respiratory Society J., vol. 42, No. 5, pp. 378-386, 2004, with partial English language translation.
Hong-Shen et al., Abstract of Chinese Journal of Tuberculosis and Respiratory Diseases (2009), vol. 32, No. 3, pp. 177-181.
Japanese Decision to Grant Patent for Application No. 2015-504803, dated Dec. 1, 2015, with English language translation.
Japanese Notification of Reasons for Refusal for Application No. 2015-504803, dated Jun. 23, 2015, with English language translation.
Japanese Notification of Reasons for Refusal for Application No. 2015-504803, dated Sep. 29, 2015, with English language translation.
Jenny T. Mao, et al., "Lung Cancer chemoprevention: current status and future directions", Curr. Respir. Care Rep., vol. 1, pp. 9-20, 2012.
Kim et al., Arterioscler. Thromb. Vasc. Biol., 2009, vol. 29, No. 6, pp. 915-920.
Magnusson Cancer Research 2007, vol. 67, No. 19, Oct. 1, 2007.
Masako Nozaki, et al., "Cysteinyl Leukotriene Receptor Antagonists Inhibit Tumor Metastasis by Inhibitiing Capillary Permeability", Keio J. Med., vol. 59, No. 1; pp. 10-18, 2010.
Matsuyama, Molecular Medicine Reports (2010), vol. 3, No. 2, pp. 245-251.
NIH Clinical Trials, Identification No. NCT00056004, dated Mar. 13, 2012, pp. 1-6.

(Continued)

*Primary Examiner* — Nizal S Chandrakumar
(74) *Attorney, Agent, or Firm* — Birch, Stewart, Kolasch & Birch, LLP

(57) ABSTRACT

Pharmaceuticals which are effective for treatment, prevention, and the like of cancer and have less side effects are disclosed. The antitumor agent of the present invention comprises as an effective ingredient at least one leukotriene inhibitor. Examples of the leukotriene inhibitor includes leukotriene production inhibitors and leukotriene receptor antagonists, and preferred specific examples of the leukotriene inhibitor include montelukast, zafirlukast, pranlukast, and zileuton; pharmaceutically acceptable salts of these compounds; and pharmaceutically acceptable solvates of these compounds and the salts. The leukotriene inhibitor can also be used as a relieving agent for pain accompanying a tumor(s), and as a stromal hyperplasia inhibitor.

6 Claims, 14 Drawing Sheets

(56) References Cited

OTHER PUBLICATIONS

Nozaki, Keio, J. Med. vol. 59, No. 1, pp. 10-18, Mar. 2010.
Prostaglandins and Other Lipid Mediators, 2012, vol. 99, Nos. 3-4, pp. 131-139.
Savari et al., PLoS One, 2013, vol. 8, No. 9: e73466. doi:10.1371/journal.pone.0073466.
Schain et al., International Journal Cancer; vol. 123, pp. 2285-2293, 2008.
Sjölander et al., "Abstract 2721: Growth of HCT-116 colon cancer xenografts is inhibited by CysLT1R antagonists.," AACR 104th Annual Meeting, Washington, DC, Apr. 6-10, 2013 (Cancer Research, vol. 73, Issue 8 Suppl., Published Apr. 15, 2013), pp. 1-3, XP009192304, abstract provided only.
Svari et al., World Journal Gastroenterol; Jan. 28, 2014; vol. 20, No. 4, pp. 968-977.
Sveinbjornsson, FASEB Journal (2008), vol. 22, No. 10, pp. 3525-3536, 10.1096/fj.07-103457.
Tan et al., "Preventive Effects of Zafirlukast on Colorectal Cancer Induced by Azoxymethane in Rats," Chinese Journal of Clinical Research, Oct. 2010, vol. 23, No. 10, pp. 847-849 (9 pages), with an English translation.
Tong et al., Clin. Cancer Res., 2002, vol. 8, No. 10, pp. 3232-3242.
Wang et al., Nat. Rev. Cancer; Mar. 2010; vol. 10, No. 3, pp. 181-193.
Zhang et al., Neuroscience Letters, vol. 363, 2004, pp. 247-251.

\* cited by examiner

ANTITUMOR AGENT

This application is a Continuation of application Ser. No. 15/680,493, filed on Aug. 18, 2017, which was filed as Continuation of application Ser. No. 14/786,089, filed on Oct. 21, 2015 (now U.S. Pat. No. 9,775,836, issued on Oct. 3, 2017), which was filed as PCT International Application No. PCT/JP2014/061264 on Apr. 22, 2014, which claims priority under 35 U.S.C. § 119(a) to Patent Application No. 2013-089356, filed in JAPAN on Apr. 22, 2013, all of which are hereby expressly incorporated by reference into the present application.

TECHNICAL FIELD

The present invention relates to an antitumor agent, a relieving agent for pain accompanying a tumor(s), and a stromal hyperplasia inhibitor, comprising a leukotriene inhibitor as an effective ingredient.

BACKGROUND ART

Cancer is a disease that accounts for a large proportion of causes of death in contemporary Japanese. A variety of anticancer agents have been developed and practically used so far, but the anticancer agents have strong side effects, and their burden to the bodies of patients is large. In recent years, heavy particle radiotherapy has been practically used, but the cost of the therapy is high, and the therapy is available only in limited facilities. Thus, heavy particle radiotherapy cannot be said to be a general option that can be freely selected at present. Therefore, anticancer agents which are highly effective against cancer, have only small side effects, and can be provided at low cost, are still strongly demanded.

As an example of a low-cost anticancer agent, an antitumor agent containing as an effective ingredient an antiallergic agent oxatomide or azelastine, or a pharmaceutically acceptable salt thereof, is disclosed in Patent Document 1. Both oxatomide and azelastine are agents classified as histamine H1 receptor antagonists. The antitumor uses of oxatomide and azelastine and pharmaceutically acceptable salts thereof described in Patent Document 1 are, more specifically, therapeutic uses for malignant tumors. Patent Document 1 does not disclose at all that leukotriene inhibitors such as leukotriene receptor antagonists are actually effective for various epithelial and nonepithelial tumors which have been spontaneously developed in vivo while producing few side effects. Patent Document 1 also does not disclose an effect on benign tumors. Moreover, Patent Document 1 does not at all describe actions of oxatomide and azelastine on stromal components such as nerves, blood vessels, and fibroblasts in tumor sites.

PRIOR ART DOCUMENT(S)

Patent Document(s)

Patent Document 1: JP 2003-252763 A

SUMMARY OF THE INVENTION

Problems to be Solved by the Invention

An object of the present invention is to provide pharmaceuticals which are effective for treatment, prevention, and the like of cancer and have less side effects.

Means for Solving the Problems

As a result of intensive study, the present inventors discovered that leukotriene inhibitors are effective for tumors spontaneously developed in vivo, and hardly produce side effects. Moreover, since degeneration of peripheral nerve cells in tumor sites was found in groups treated with a leukotriene inhibitor, leukotriene inhibitors were found to be also effective for relieving pain accompanying tumors. In addition, the present inventors carried out immunostaining of tissue samples of various human-derived tumors as well as spontaneously-developed rat tumor tissues using an antibody against leukotriene receptors. As a result, the presence of cells positive for the leukotriene receptor antibody could be found in all of the various tumor tissues investigated, irrespective of whether the tumor is epithelial or nonepithelial and whether the tumor is malignant or benign. Thus, the leukotriene inhibitors have been confirmed to be effective for various tumors, thereby completing the present invention.

That is, the present invention provides an antitumor agent comprising at least one leukotriene inhibitor as an effective ingredient. The present invention also provides a relieving agent for pain accompanying a tumor(s), which agent comprises at least one leukotriene inhibitor as an effective ingredient. The present invention also provides a stromal hyperplasia inhibitor comprising at least one leukotriene inhibitor as an effective ingredient. The present invention also provides a method for treatment, prevention, metastasis suppression, or recurrence suppression of a tumor(s) in a subject in need thereof, which method comprises administering an effective amount of at least one leukotriene inhibitor to the subject. The present invention also provides a method for relieving pain accompanying a tumor(s) in a subject in need thereof, which method comprises administering an effective amount of at least one leukotriene inhibitor to the subject. The present invention also provides a method for inhibiting stromal hyperplasia in a subject in need thereof, which method comprises administering an effective amount of at least one leukotriene inhibitor to the subject. The present invention also provides a leukotriene inhibitor for use in treatment, prevention, metastasis suppression, or recurrence suppression of a tumor(s). The present invention also provides a leukotriene inhibitor for use in relieving pain accompanying a tumor(s). The present invention also provides a leukotriene inhibitor for use in inhibiting stromal hyperplasia. The present invention also provides a method for screening of an antitumor agent, a relieving agent for pain accompanying a tumor(s), or a stromal hyperplasia inhibitor, which method uses as an indicator an ability to inhibit a signaling pathway mediated by binding of leukotriene to a leukotriene receptor. The present invention also provides a method for producing an antitumor agent, a relieving agent for pain accompanying a tumor(s), or a stromal hyperplasia inhibitor, which method comprises the steps of: screening of an antitumor agent, a relieving agent for pain accompanying a tumor(s), or a stromal hyperplasia inhibitor by the screening method according to the above-described present invention; and producing the antitumor agent, the relieving agent for pain accompanying a tumor(s), or the stromal hyperplasia inhibitor obtained by the screening.

Effect of the Invention

The antitumor agent of the present invention has been confirmed to be actually effective for tumors spontaneously developed in vivo, and to hardly produce side effects. Since leukotriene inhibitors practically used as antiallergic agents can be used as effective ingredients, the antitumor agent of the present invention can be provided at low cost. The present inventors revealed that leukotriene receptors are expressed in various tumors irrespective of whether the tumor is epithelial or nonepithelial, and whether malignant or benign (see Examples below). Leukotriene inhibitors can exert their antitumor effects against various tumors by inhibiting signal transduction mediated by leukotriene receptors in tumor sites by actions such as an antagonistic action on leukotriene receptors or inhibition of leukotriene production.

MODE FOR CARRYING OUT THE INVENTION

Figure 1:
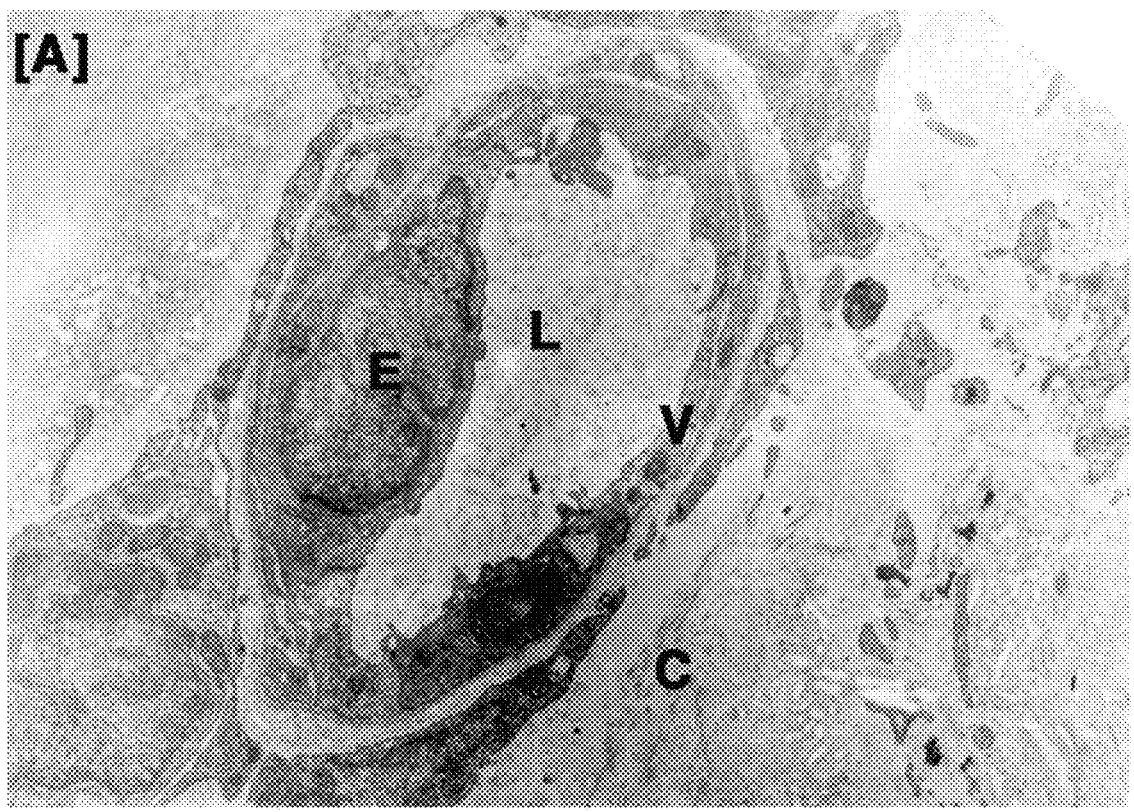
FIG. 1 is an electron micrograph of a tumor tissue of the untreated tumor-bearing rat group (Comparative Example 1). E, vascular endothelial cell; L, intravascular lumen; V, blood vessel; C, collagen fiber.

In the present invention, the "leukotriene inhibitor" is a substance that inhibits a signaling pathway mediated by binding of leukotriene to a leukotriene receptor. The inhibition may occur in any step along the pathways from biosynthesis of leukotriene to the signaling pathways located downstream of the leukotriene receptor. Possible specific examples of the leukotriene inhibitor include substances that inhibit production of leukotriene, substances that inhibit binding of leukotriene to a leukotriene receptor, and substances that suppress activation of leukotriene receptors to inhibit signal transduction to the downstream factors. Typically, the leukotriene inhibitor may be a substance that inhibits or suppresses a function of leukotriene in vivo, and includes leukotriene production inhibitors and leukotriene receptor antagonists.

In the present invention, examples of the "leukotriene production inhibitors" include substances that inhibit factors such as enzymes that function in a leukotriene biosynthetic pathway (leukotriene biosynthesis inhibitors), and substances that inhibit release of leukotriene from cells which produce leukotriene, such as mast cells, eosinophils, neutrophils, basophils, and monocytes (leukotriene release inhibitors). Specific examples of leukotriene production inhibitors that may be used in the present invention include 5-lipoxygenase inhibitors such as zileuton, ABT-761, CJ-13610, ZD-2138, AA-861, and cirsiliol; inhibitors of 5-lipoxygenase-activating proteins, such as MK-886 and BAY X1005. Pharmaceutically acceptable salts of these compounds, and pharmaceutically acceptable solvates of these compounds and salts thereof may also be used. However, the leukotriene production inhibitors that may be used as effective ingredients in the present invention are not limited to these specific examples.

In the present invention, the "leukotriene receptor antagonists" include various substances that antagonistically function against the action of leukotriene on a leukotriene receptor. Examples of the leukotriene receptor antagonists include substances that competitively or noncompetitively inhibit binding of leukotriene to a leukotriene receptor, and substances having an action to suppress activation of a leukotriene receptor, to inhibit signal transduction to the downstream factors. Examples of the "leukotriene receptor antagonists" also include molecules such as inverse agonists which bind to a leukotriene receptor to stabilize the receptor into an inactive structure, which are one example of antagonists. Specific examples of the leukotriene receptor antagonists that may be used in the present invention include zafirlukast, montelukast, pranlukast, FPL55712, BAYu9773, LY293111 Na, CGS 25019C, ONO-4057, SB201993, CP195543, SC53228, and BIIL 284 (BIIL 260). Pharmaceutically acceptable salts of these compounds, and pharmaceutically acceptable solvates of these compounds and salts thereof may also be used. However, the leukotriene receptor antagonists that may be used as effective ingredients in the present invention are not limited to these specific examples.

Examples of the pharmaceutically acceptable salts include acid addition salts such as hydrochloric acid salt, sulfuric acid salt, fumaric acid salt, maleic acid salt, tartaric acid salt, and citric acid salt. In cases where the leukotriene inhibitor is an acid, examples of the pharmaceutically acceptable salts also include metal salts such as sodium salt, potassium salt, and calcium salt. Examples of the pharmaceutically acceptable solvates include solvates with an organic solvent, and hydrates. However, the pharmaceutically acceptable salts and the pharmaceutically acceptable solvates are not limited to these specific examples.

Preferred specific examples of the leukotriene inhibitor include at least one selected from the group consisting of: compounds selected from montelukast, zafirlukast, pranlukast, and zileuton; pharmaceutically acceptable salts of the compounds; and pharmaceutically acceptable solvates of the compounds and the salts of the compounds.

In the present invention, the term "antitumor" includes suppression of tumorigenesis (initiation, metastasis, and recurrence) and suppression of tumor proliferation. Accordingly, the "antitumor agent" includes therapeutic agents, preventive agents, metastasis-suppressing agents, and recurrence-suppressing agents for tumors. The term "tumor" includes both benign tumors and malignant tumors. More specifically, the tumor can be classified into malignant epithelial tumors, benign epithelial tumors, malignant nonepithelial tumors, and benign nonepithelial tumors. Examples of the malignant tumors (cancers) include solid cancers and blood cancers. Examples of the solid cancers include carcinomas (malignant epithelial tumors), sarcomas (malignant nonepithelial tumors), and nervous system malignant solid tumors such as melanoma and glioma (malignant nonepithelial tumors). Examples of the blood cancers include blood malignant tumors such as leukemia, malignant lymphoma, and multiple myeloma. The term "solid tumor" includes not only solid cancers, but also benign solid tumors.

The antitumor agent of the present invention comprises at least one leukotriene inhibitor as an effective ingredient. The antitumor agent may comprise two or more leukotriene inhibitors as effective ingredients. In cases where the antitumor agent of the present invention is used for treatment of malignant tumors, agents containing as an effective ingredient at least one selected from oxatomide and azelastine and pharmaceutically acceptable salts thereof may be excluded from the antitumor agent of the present invention irrespective of whether or not these antiallergic agents are included in the leukotriene inhibitor defined in the present invention. In cases where the antitumor agent of the present invention is used as a metastasis-suppressing agent or a recurrence-suppressing agent for malignant tumors, agents comprising as an effective ingredient at least one selected from oxatomide and azelastine and pharmaceutically acceptable salts thereof may be excluded from the antitumor agent of the present invention. In cases where the antitumor agent of the present invention is used as a preventive agent for malignant tumors, agents comprising as an effective ingredient at least one selected from oxatomide and azelastine and pharmaceutically acceptable salts thereof may be excluded from the antitumor agent of the present invention.

As described in Examples below, expression of leukotriene receptors has been confirmed in various types of tumors irrespective of whether the tumor is benign or malignant, and whether epithelial or nonepithelial. Leukotriene inhibitors are thought to exert their antitumor effects by inhibiting signal transduction mediated by leukotriene receptors expressed in the tumor site, by an antagonistic action against the leukotriene receptors or by inhibition of leukotriene production. Thus, leukotriene inhibitors can exert their antitumor effect widely against malignant and benign epithelial tumors, and malignant and benign nonepithelial tumors. The antitumor agent of the present invention can be preferably used for, e.g., solid tumors, or malignant tumors, or solid cancers, although uses of the antitumor agent are not limited thereto.

Leukotriene inhibitors have an action to induce apoptosis of tumor cells spontaneously developed in vivo (see Examples below). In particular, since apoptosis and degeneration are also found not only in endothelial cells of newly formed blood vessels, which are stromal components of tumor tissues and indispensable as routes for supplying enzymes and nutrients to tumor cells, but also in other stromal cells such as peripheral nerve cells that proliferate side by side with newly formed blood vessels in tumor sites and smooth muscle cells involved in the contractile motion of blood vessels, leukotriene inhibitors can be preferably used for solid tumors, especially solid cancers, among tumors.

Induction of apoptosis of endothelial cells of newly formed blood vessels by a leukotriene inhibitor is found only in blood vessels in solid tumor tissues, and not found in non-tumor healthy tissues. From the viewpoint of this effect, the antitumor agent of the present invention used for solid tumors can also be said to be an angiogenesis inhibitor specific to solid tumors. From the viewpoint of the inhibitory action against hyperplasia of stromal cells, the agent can also be said to be a stromal hyperplasia inhibitor specific to solid tumors. Newly formed blood vessels are indispensable as routes for supplying enzymes and nutrients to tumor cells, and other stromal components such as fibroblasts, collagen fibers produced by fibroblasts, peripheral nerve cells, and smooth muscle cells constitute a tumor site together with the tumor cells. Since a leukotriene inhibitor can suppress the growth and metastasis of a solid tumor by blocking the routes for supplying enzymes and nutrients to tumor cells and killing proliferated stromal cells, treatment and prevention of solid tumors (including prevention of metastasis and recurrence of malignant tumors) are possible.

However, since, as described above, induction of apoptosis by a leukotriene inhibitor can be found not only for newly formed blood vessels, but also for tumor cells themselves, the effect of the antitumor agent of the present invention is not limited to solid tumors, and the agent is also effective for blood cancers.

In general, in cases where a patient is judged as being suspected of having a cancer in medical examination or health screening, and then is found to have a benign tumor as a result of detailed examination, the patient is followed up thereafter by regularly visiting a hospital for the purpose of early detection and treatment of malignant change (canceration). Since leukotriene inhibitors exert their therapeutic effects such as growth inhibition also on benign tumors, leukotriene inhibitors are also useful for prevention of tumors (more specifically, malignant tumors). In cases where the antitumor agent is used for the purpose of prevention, the agent may be typically administered to a subject having a benign tumor, more specifically, a subject having a benign tumor which may undergo malignant change.

Since leukotriene inhibitors cause degeneration of peripheral nerve cells in tumor sites and kill proliferated nerve cells in the tumor sites, leukotriene inhibitors are also effective for relieving pain accompanying tumors.

As described above, various leukotriene inhibitors are known, and methods for synthesizing these leukotriene inhibitors are also known.

The administration route of the antitumor agent of the present invention may be oral administration or parenteral administration (e.g. intravenous administration, subcutaneous administration, intramuscular administration, rectal administration or the like), and may be systemic administration or topical administration. Oral administration is preferred from the viewpoint of simplicity. The dose/dosage is appropriately set depending on the severity of symptoms (for example, the tumor size, the degree of progression, and/or the malignancy) in the patient, the type of the leukotriene inhibitor used, and the like. Although an antitumor effect can be obtained at a dose/dosage at which the agent is used as an antiallergic agent, the antitumor agent may be administered, if necessary, at a dose/dosage 10 to 100 times higher than that for use as an antiallergic agent, or at an even higher dose/dosage. The antitumor agent of the present invention may be used at an amount of about 1 mg to 200,000 mg, for example, about 10 mg to 100,000 mg, about 100 mg to 100,000 mg, about 10 mg to 50,000 mg, about 100 mg to 50,000 mg, or about 10 mg to 10,000 mg in terms of the amount of the leukotriene inhibitor per adult per day, although the dose/dosage is not limited to these.

The dosage form of the antitumor agent is not limited, and may be appropriately selected depending on the administration route. The antitumor agent can be produced by formulation techniques commonly used in the field of pharmaceuticals. The antitumor agent of the present invention may have the same constitution as that of a formulation commercially available as an antiallergic agent.

The subject to which the leukotriene inhibitor is administered is a mammal, and examples of the mammal include, but are not limited to, human, dog, cat, rabbit, hamster, mouse, rat, ferret, horse, cattle, pig, sheep, and monkey.

By using as an indicator the ability to inhibit a signaling pathway mediated by binding of leukotriene to a leukotriene receptor, screening of a novel antitumor agent, a relieving agent for pain accompanying a tumor(s), or a stromal hyperplasia inhibitor can be carried out. The inhibition of a signaling pathway mediated by binding of leukotriene to a leukotriene receptor may be, as described above, inhibition of leukotriene production, inhibition of binding of leukotriene to a leukotriene receptor, suppression of activation of a leukotriene receptor to inhibit signal transduction to the downstream factors, or the like. Whether or not an agent has an action to inhibit the signaling pathway can be investigated based on, for example, whether or not the agent inhibits the function of a promotional factor in the signaling pathway, or whether or not the agent promotes the function of a suppressive factor in the signaling pathway. The inhibition of the function of the promotional factor may be, for example, inhibition of expression of the factor in the cell, or inhibition of a physiological activity of the factor. The promotion of the function of the suppressive factor may be, for example, promotion of expression of the factor in the cell, or promotion of a physiological activity of the factor.

EXAMPLES

The present invention is concretely described below by way of Examples. However, the present invention is not limited to the Examples below.

Materials

Sprague-Dawley rats which had spontaneously developed a tumor during breeding (hereinafter referred to as tumor-bearing rats) were purchased from Charles River Japan, Inc., and used for experiments. Tumors observed were all mammary gland tumors (adenocarcinoma and adenoma). All of these were spontaneous tumors, and the rats were cancerbearing animals having various conditions of tumorigenesis including carcinogenic factors in mammals including human.

Methods

Comparative Example 1: Observation of Tumor Lesion Samples from Untreated Tumor-Bearing Rats (3 Cases)

Under ether anesthetization, tumor tissues were removed from tumor-bearing rats. The removed tumors were fixed, and thereafter samples for light microscopy (hematoxylin-eosin staining) and samples for electron microscopy (uranium-lead double staining) were prepared and observed.

Example 1: Therapeutic Effect of Montelukast Sodium on Tumor-Bearing Rats (3 Cases)

To tumor-bearing rats, a leukotriene inhibitor containing montelukast sodium as an active ingredient (leukotriene receptor antagonist; trade name "Singulair Tablets"; manufactured by MSD K. K.) was orally administered for up to 7 days at a daily dose of 0.16 mg/kg body weight in terms of montelukast sodium. On Day 3 and Day 7, tumor tissues were removed under ether anesthetization. In the same manner as in Comparative Example 1, the removed tumors were fixed, and thereafter samples for light microscopy (hematoxylin-eosin staining) and samples for electron microscopy (uranium-lead double staining) were prepared and observed.

Example 2: Therapeutic Effect of Zafirlukast on Tumor-Bearing Rats (3 Cases)

To tumor-bearing rats, a leukotriene inhibitor containing zafirlukast as an active ingredient (leukotriene receptor antagonist; trade name "Accolate"; manufactured by Astra-Zeneca K. K.) was orally administered for up to 7 days at a daily dose of 1.33 mg/kg body weight in terms of zafirlukast. On Day 3 and Day 7, tumor tissues were removed under ether anesthetization. In the same manner as in Comparative Example 1, the removed tumors were fixed, and thereafter samples for light microscopy (hematoxylin-eosin staining) and samples for electron microscopy (uranium-lead double staining) were prepared and observed.

Example 3: Therapeutic Effect of Pranlukast Hydrate on Tumor-Bearing Rats (3 Cases)

To tumor-bearing rats, a leukotriene inhibitor containing pranlukast hydrate as an active ingredient (leukotriene receptor antagonist; trade name "Onon"; manufactured by Ono Pharmaceutical Co., Ltd.) was orally administered for up to 7 days at a daily dose of 7.5 mg/kg body weight in terms of pranlukast hydrate. On Day 3 and Day 7, tumor tissues were removed under ether anesthetization. In the same manner as in Comparative Example 1, the removed tumors were fixed, and thereafter samples for light microscopy (hematoxylin-eosin staining) and samples for electron microscopy (uranium-lead double staining) were prepared and observed.

Example 4: Therapeutic Effect of Zileuton on Tumor-Bearing Rats (3 Cases)

To tumor-bearing rats, a leukotriene inhibitor containing zileuton as an active ingredient (leukotriene biosynthesis inhibitor; trade name "ZYFLO"; manufactured by Abbott Laboratories) was orally administered for up to 7 days at a daily dose of 34.3 mg/kg body weight in terms of zileuton. On Day 3 and Day 7, tumor tissues were removed under ether anesthetization. In the same manner as in Comparative Example 1, the removed tumors were fixed, and thereafter samples for light microscopy (hematoxylin-eosin staining) and samples for electron microscopy (uranium-lead double staining) were prepared and observed.

Results

Unlike the tumor tissue images of the untreated tumor-bearing rats of Comparative Example 1, in the tumor cells in all tumor-bearing rats treated with a leukotriene inhibitor, that is, montelukast sodium (leukotriene receptor antagonist, Example 1), zafirlukast (leukotriene receptor antagonist, Example 2), pranlukast hydrate (leukotriene receptor antagonist, Example 3), or zileuton (leukotriene biosynthesis inhibitor, Example 4), apoptosis was already induced on as early as Day 3, and a remarkable inhibitory effect on the development and the growth of the tumor cells was observed.

In all the treated groups, apoptosis was induced in endothelial cells of newly formed blood vessels, which are stromal components of tumor tissues and indispensable as routes for supplying enzymes and nutrients to tumor cells. It was therefore thought that blood flow in the tumor was blocked, leading to the inhibitory effect on the development and the growth of the tumor cells. In addition to vascular endothelial cells, apoptosis was also observed in fibroblasts and smooth muscle cells, and moreover degeneration of peripheral nerve cells extending side by side with blood vessels was also found. Such apoptosis and degeneration of stromal cells were found only in tumor tissues in the treated groups, and not found in normal sites in all treated groups and tumor tissues in the untreated group.

No side effects were observed in the rats in the treated groups.

The pathological findings described above are explained below in more detail based on micrographs of pathological specimens.

FIG. 1 is an electron micrograph of a tumor tissue of the untreated group (Comparative Example 1), wherein a normal vascular endothelial cell (E in the figure) is observed.

Figure 2:
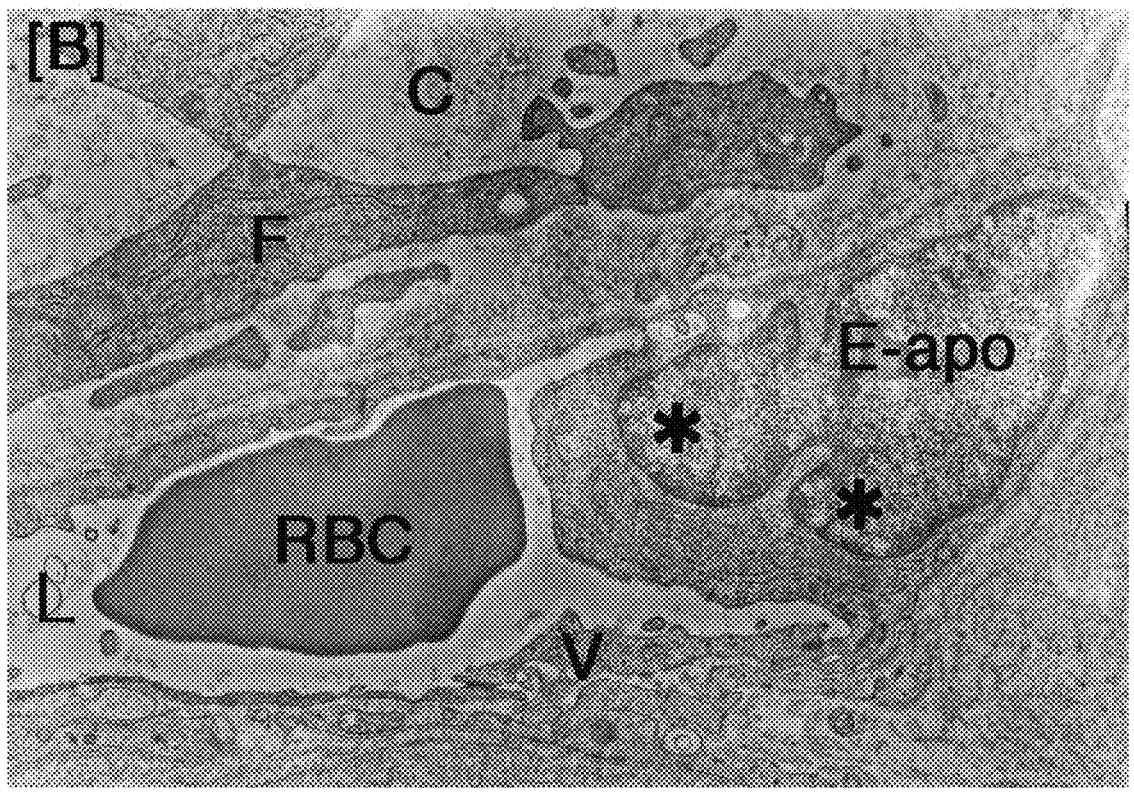
FIG. 2 is an electron micrograph of a tumor tissue of the tumor-bearing rat group with administration of montelukast sodium (Example 1; dosing period, 3 days). RBC, red blood cell; L, intravascular lumen; V, blood vessel; C, collagen fiber; F, fibroblast; E-apo, apoptosis of vascular endothelial cell.
Figure 3:
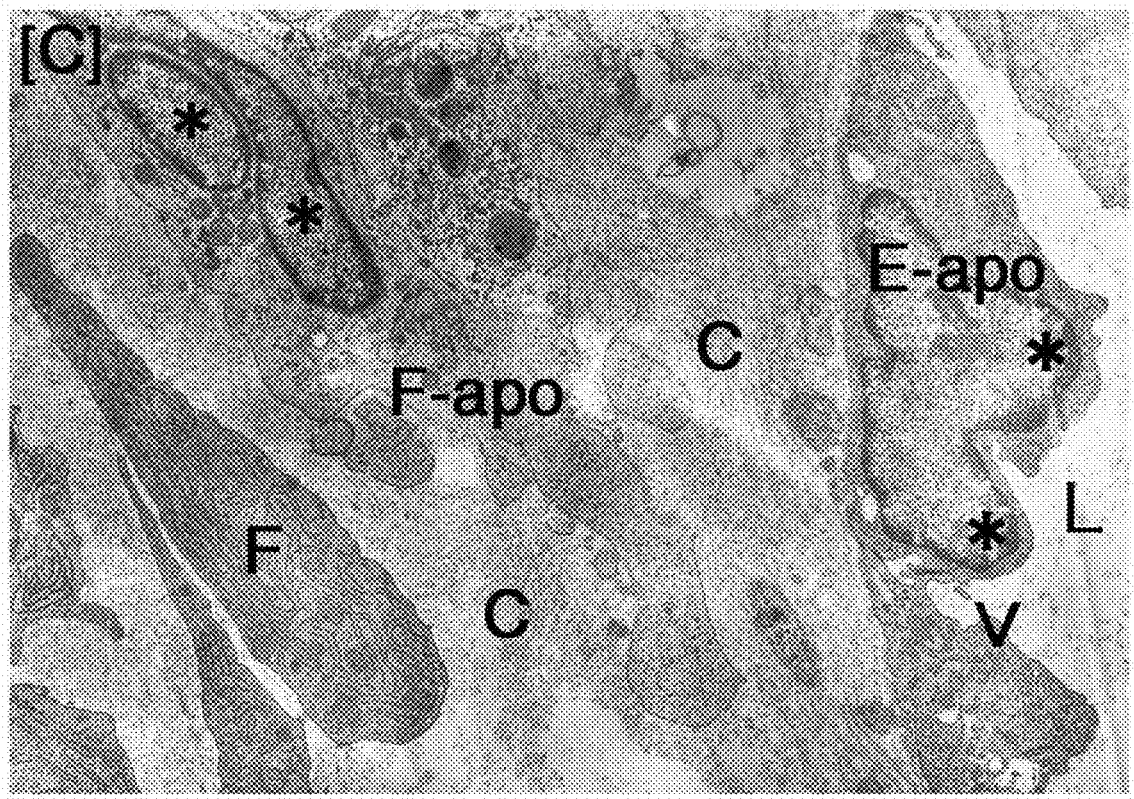
FIG. 3 is an electron micrograph of a tumor tissue of the tumor-bearing rat group with administration of montelukast sodium (Example 1; dosing period, 3 days). L, intravascular lumen; V, blood vessel; C, collagen fiber; F, fibroblast; E-apo, apoptosis of vascular endothelial cell; F-apo, apoptosis of fibroblast.

FIGS. 2 and 3 are electron micrographs of tumor tissues of the group with administration of montelukast sodium (Example 1, dosing period, 3 days). In blood vessels in the tumor tissues, apoptosis of endothelial cells (E-apo in the figures) was observed. These endothelial cells showed irregular condensation and fragmentation (* in the figures) of their nuclei. These conditions correspond to Stage II to III of apoptosis (T. Ihara, et al. The process of ultrastructural changes from nuclei to apoptotic body. Virchow Arch (1998) 433: 443-447). By the apoptosis of endothelial cells, an effect to inhibit blood flow into the tumor tissues (an inhibitory effect on newly formed blood vessels) could be obtained. Apoptosis of fibroblasts (F-apo in the figures), which produces collagen fibers and constitutes the stroma of the tumor tissue, was induced, and reduction in collagen fibers (C in the figures) was also observed. Thus, an effect to inhibit stromal hyperplasia was also seen.

Figure 4:
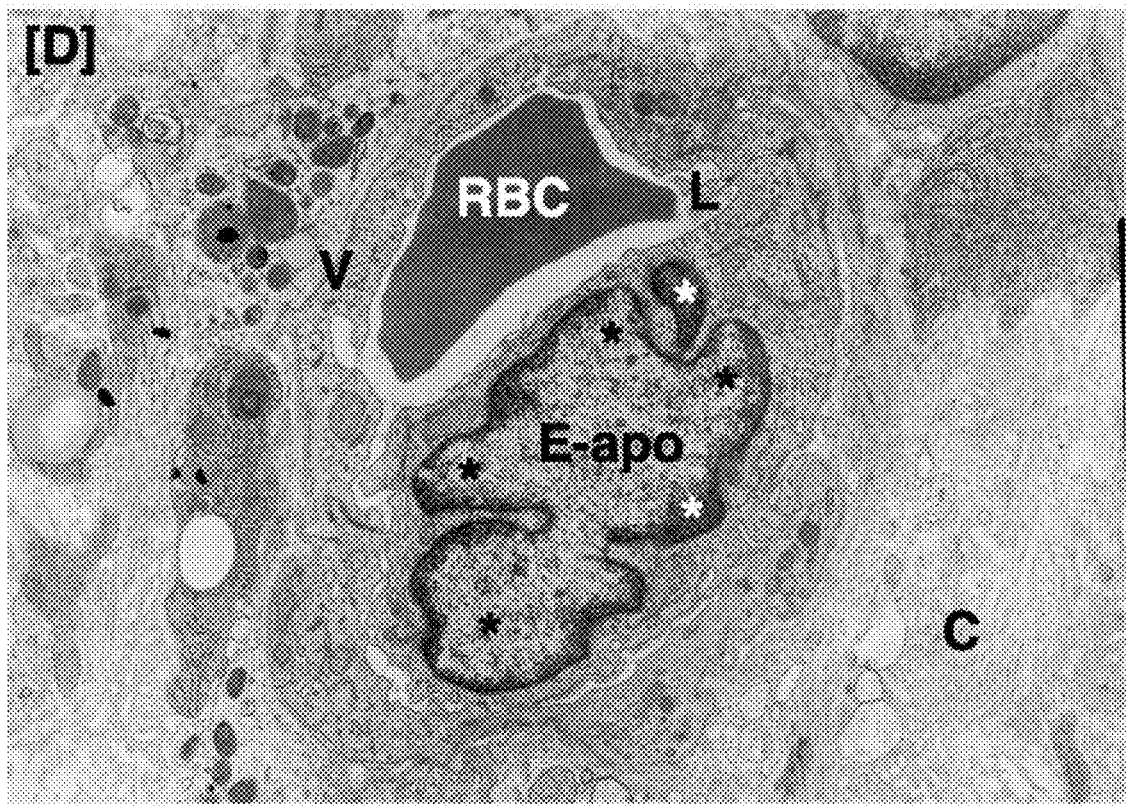
FIG. 4 is an electron micrograph of a tumor tissue of the tumor-bearing rat group with administration of pranlukast hydrate (Example 3; dosing period, 3 days). RBC, red blood cell; L, intravascular lumen; V, blood vessel; C, collagen fiber; E-apo, apoptosis of vascular endothelial cell.
Figure 5:
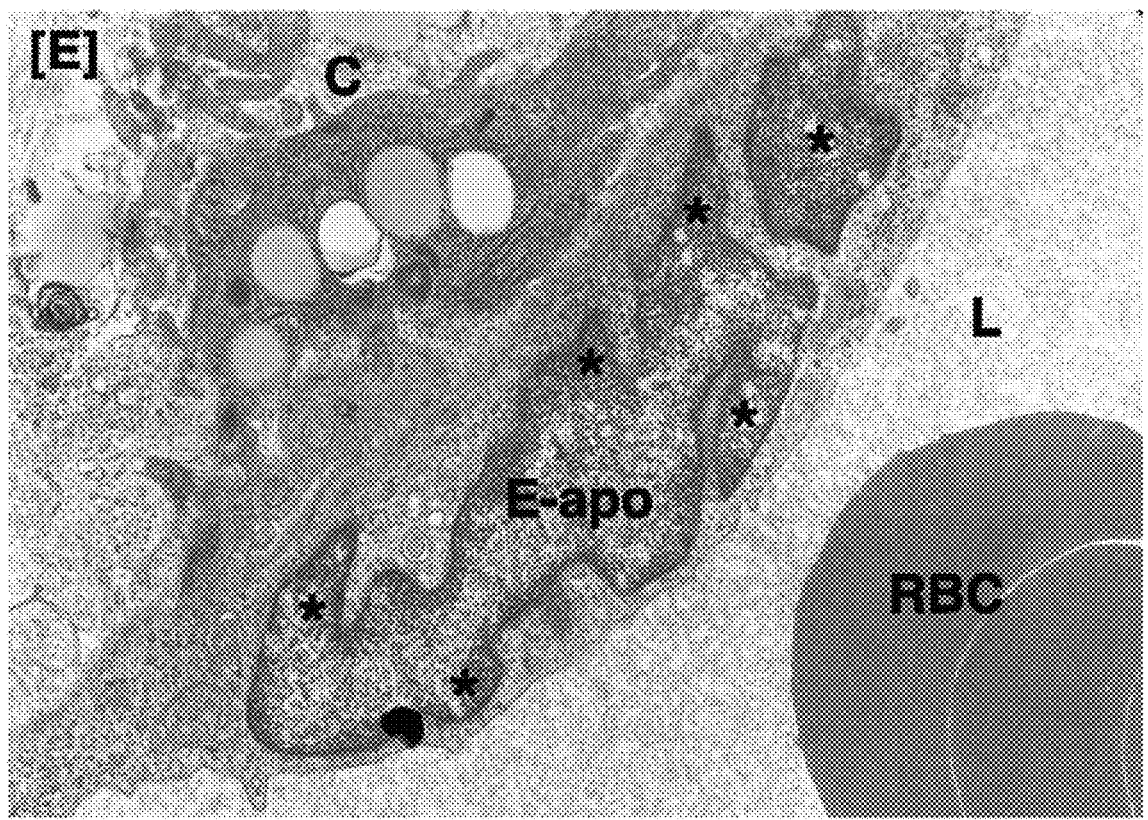
FIG. 5 is an electron micrograph of a tumor tissue of the tumor-bearing rat group with administration of pranlukast hydrate (Example 3; dosing period, 3 days). RBC, red blood cell; L, intravascular lumen; V, blood vessel; C, collagen fiber; E-apo, apoptosis of vascular endothelial cell.
Figure 6:
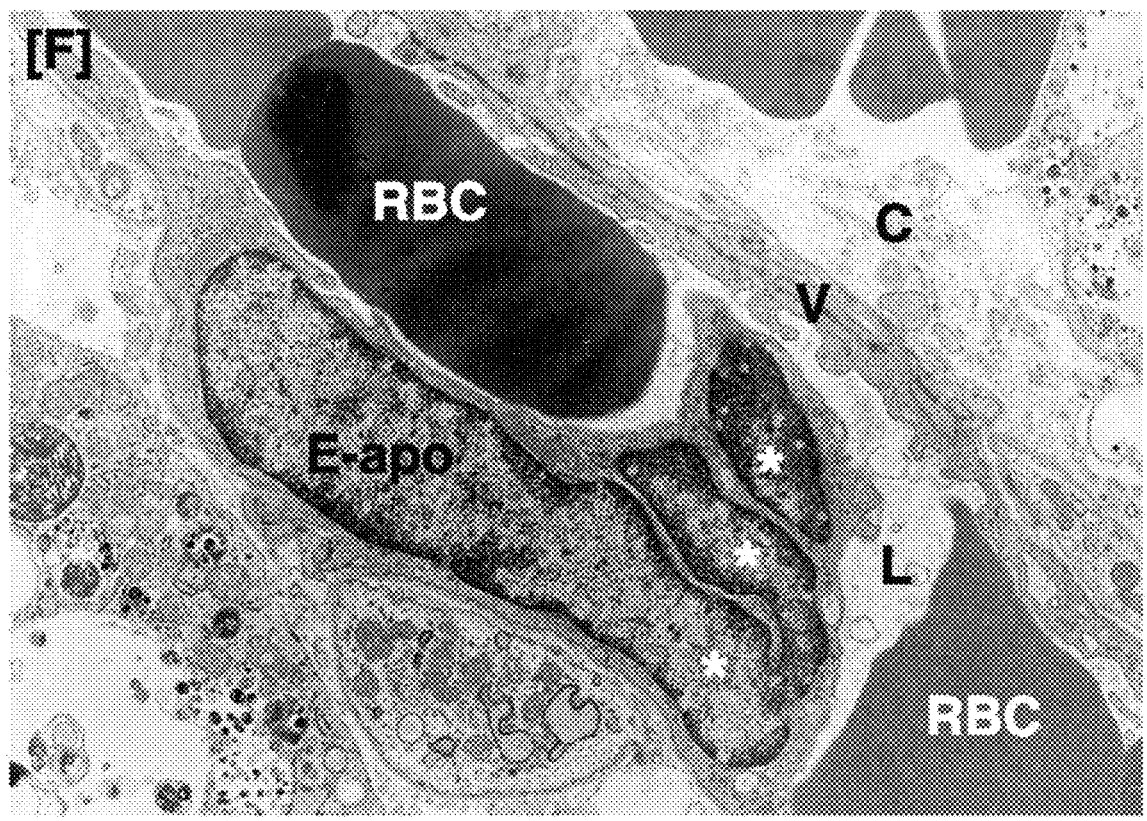
FIG. 6 is an electron micrograph of a tumor tissue of the tumor-bearing rat group with administration of pranlukast hydrate (Example 3; dosing period, 3 days). RBC, red blood cell; L, intravascular lumen; V, blood vessel; C, collagen fiber; E-apo, apoptosis of vascular endothelial cell.

FIGS. 4 to 6 are electron micrographs of tumor tissues of the group with administration of pranlukast hydrate (Example 3; dosing period, 3 days). In blood vessels in the tumor tissues, apoptosis of endothelial cells (E-apo in the figures) was observed. These endothelial cells showed irregular condensation and fragmentation (* in the figures) of their nuclei. These conditions correspond to Stage II to III of apoptosis (T. Ihara, et al. 1998, described above). Similarly to the group with administration of zileuton, an effect to inhibit blood flow into the tumor tissues by apoptosis of endothelial cells (an inhibitory effect on newly formed blood vessels) could be obtained.

Figure 7:
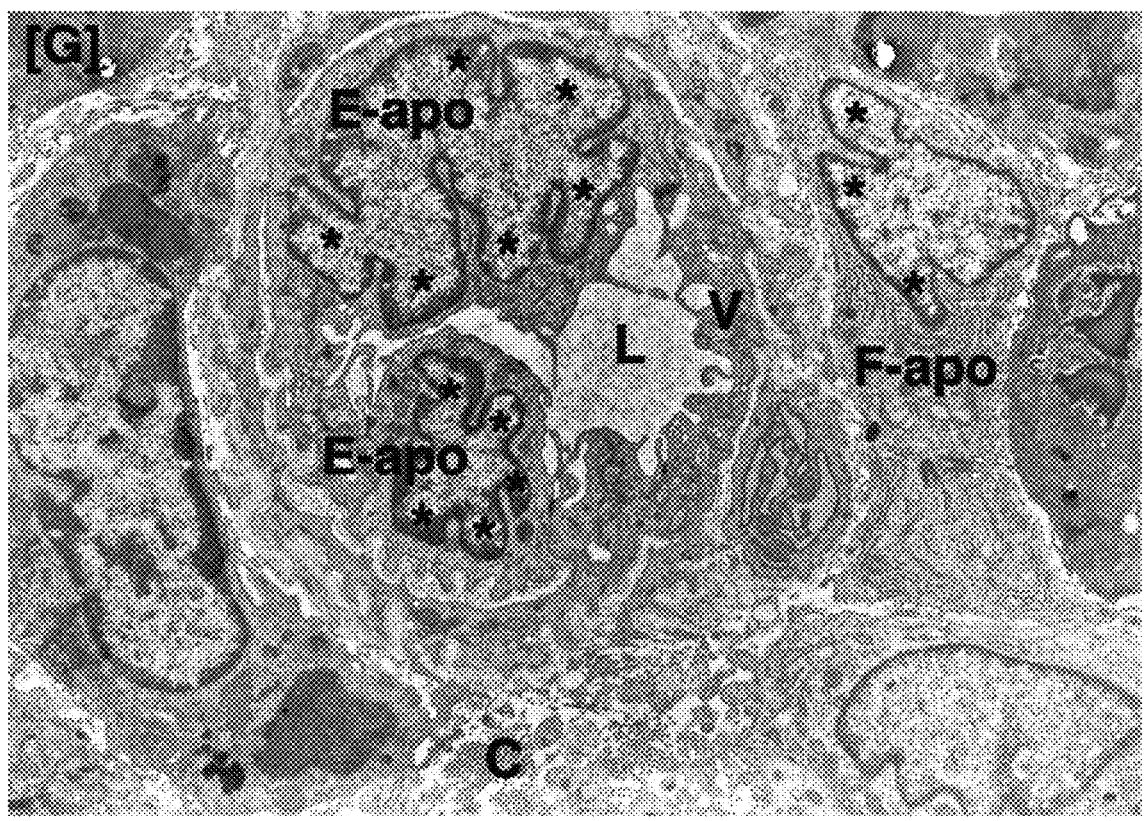
FIG. 7 is an electron micrograph of a tumor tissue of the tumor-bearing rat group with administration of zafirlukast (Example 2; dosing period, 3 days). RBC, red blood cell; L, intravascular lumen; V, blood vessel; C, collagen fiber; E, vascular endothelial cell; F, fibroblast; E-apo, apoptosis of vascular endothelial cell; F-apo, apoptosis of fibroblast.
Figure 8:
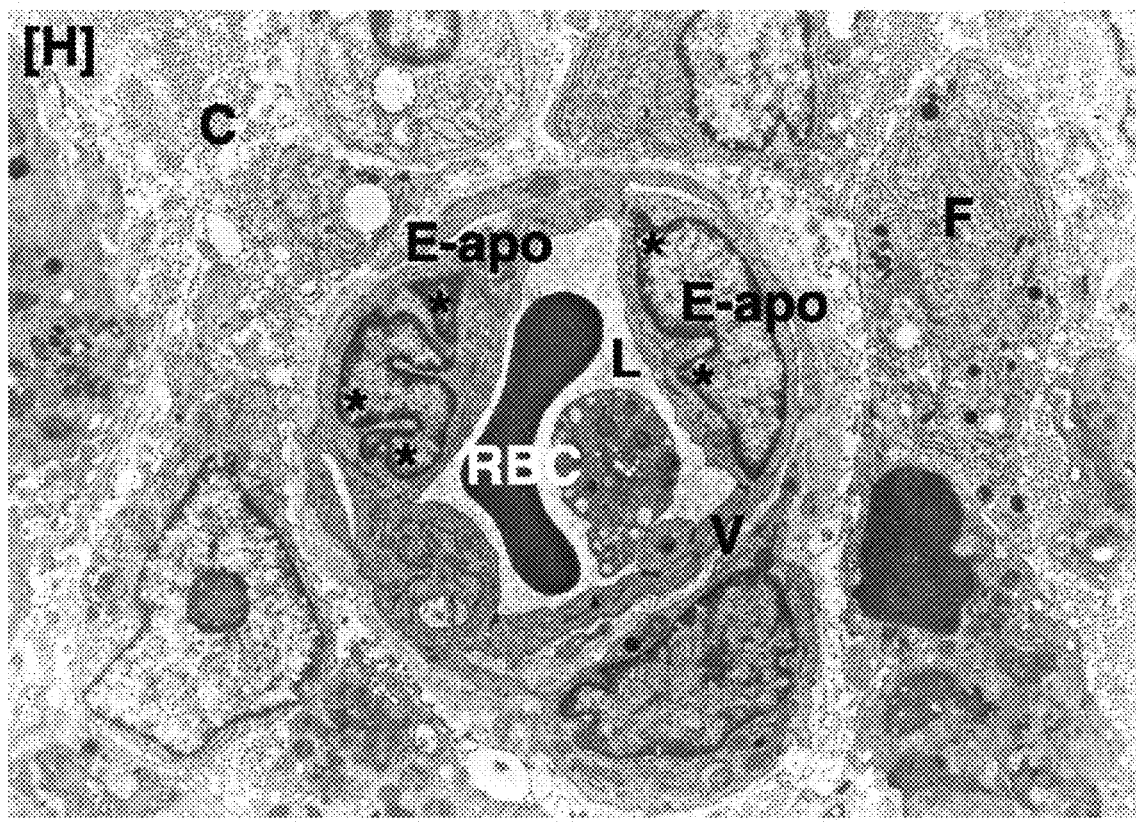
FIG. 8 is an electron micrograph of a tumor tissue of the tumor-bearing rat group with administration of zafirlukast (Example 2; dosing period, 3 days). RBC, red blood cell; L, intravascular lumen; V, blood vessel; C, collagen fiber; F, fibroblast; E-apo, apoptosis of vascular endothelial cell.
Figure 9:
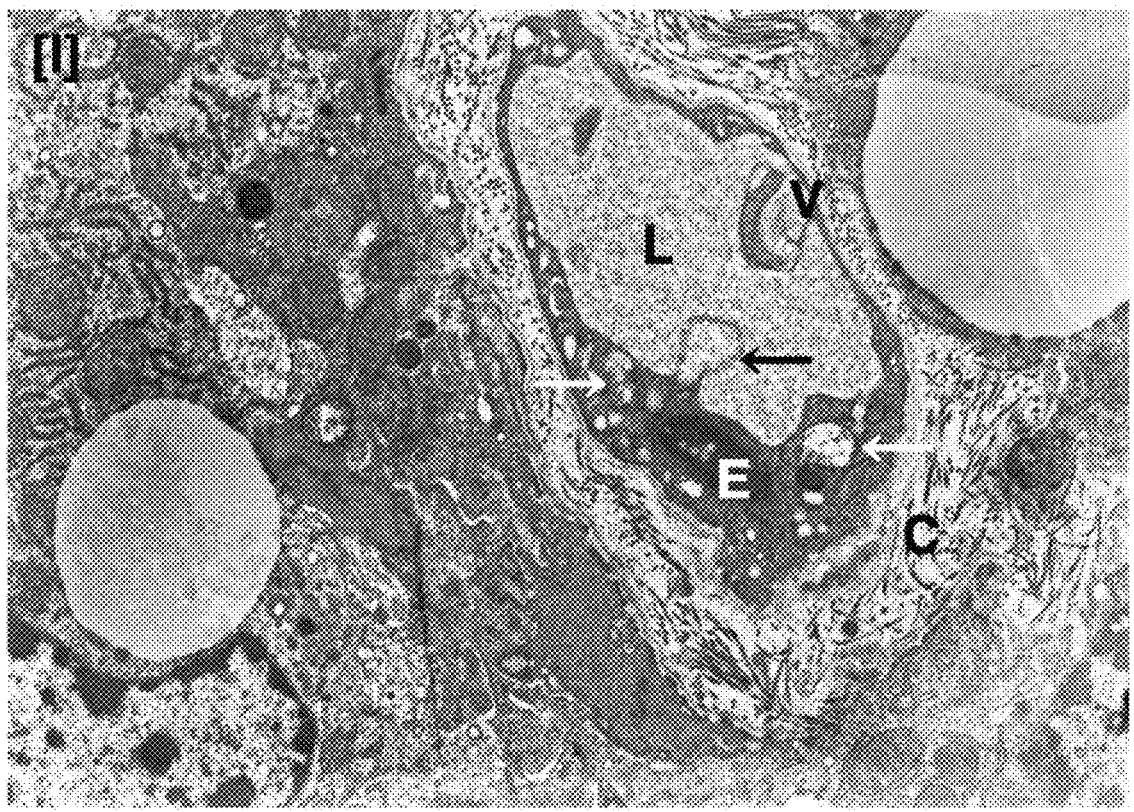
FIG. 9 is an electron micrograph of a tumor tissue of the tumor-bearing rat group with administration of zafirlukast (Example 2; dosing period, 3 days). L, intravascular lumen; V, blood vessel; C, collagen fiber; E, vascular endothelial cell.

FIGS. 7 to 9 are electron micrographs of tumor tissues of the group with administration of zafirlukast (Example 2; dosing period, 3 days). In blood vessels in the tumor tissues, apoptosis of endothelial cells (E-apo in the figures) was observed. These endothelial cells showed irregular condensation and fragmentation (* in the figures) of their nuclei. These conditions correspond to Stage II to III of apoptosis (T. Ihara, et al. 1998, described above). In addition, degeneration (→) of vascular endothelial cells (E) was observed (FIG. 9). By the apoptosis and the degeneration of endothelial cells, an effect to inhibit blood flow into the tumor tissues (an inhibitory effect on newly formed blood vessels) could be obtained.

Figure 10:
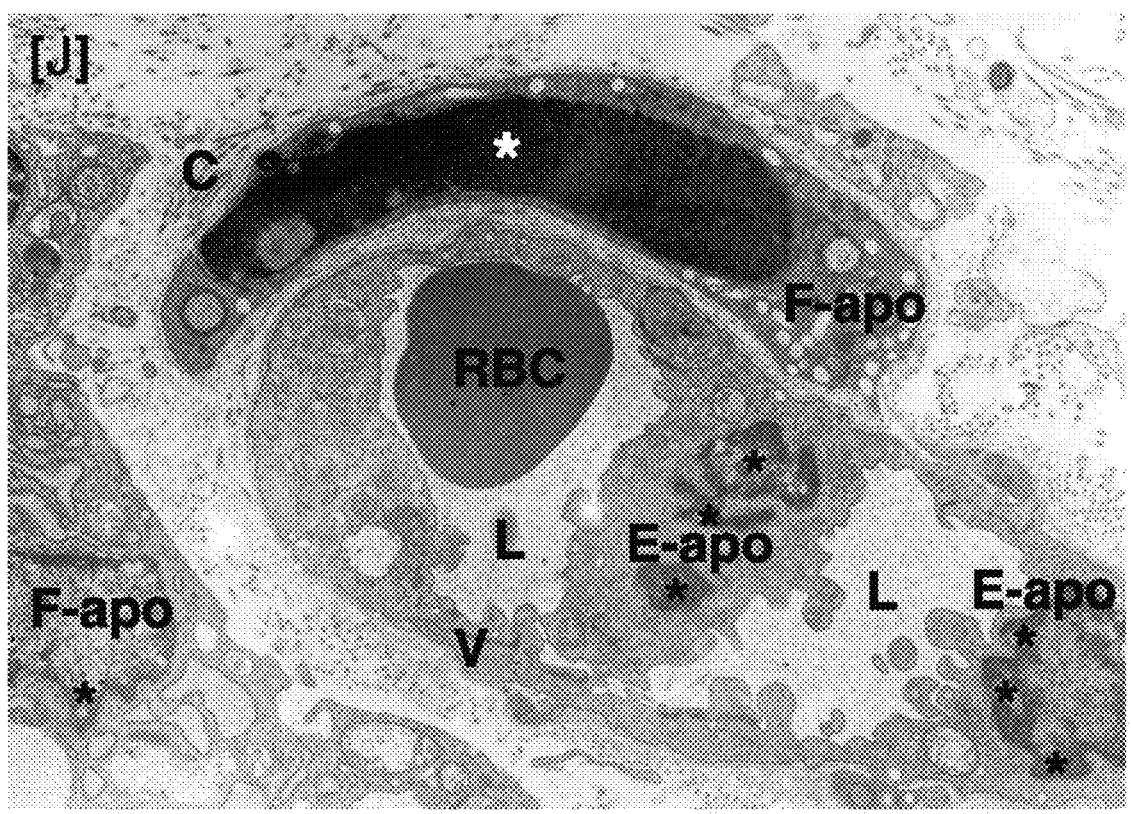
FIG. 10 is an electron micrograph of a tumor tissue of the tumor-bearing rat group with administration of zileuton (Example 4; dosing period, 3 days). RBC, red blood cell; L, intravascular lumen; V, blood vessel; C, collagen fiber; E-apo, apoptosis of vascular endothelial cell; F-apo, apoptosis of fibroblast.
Figure 11:
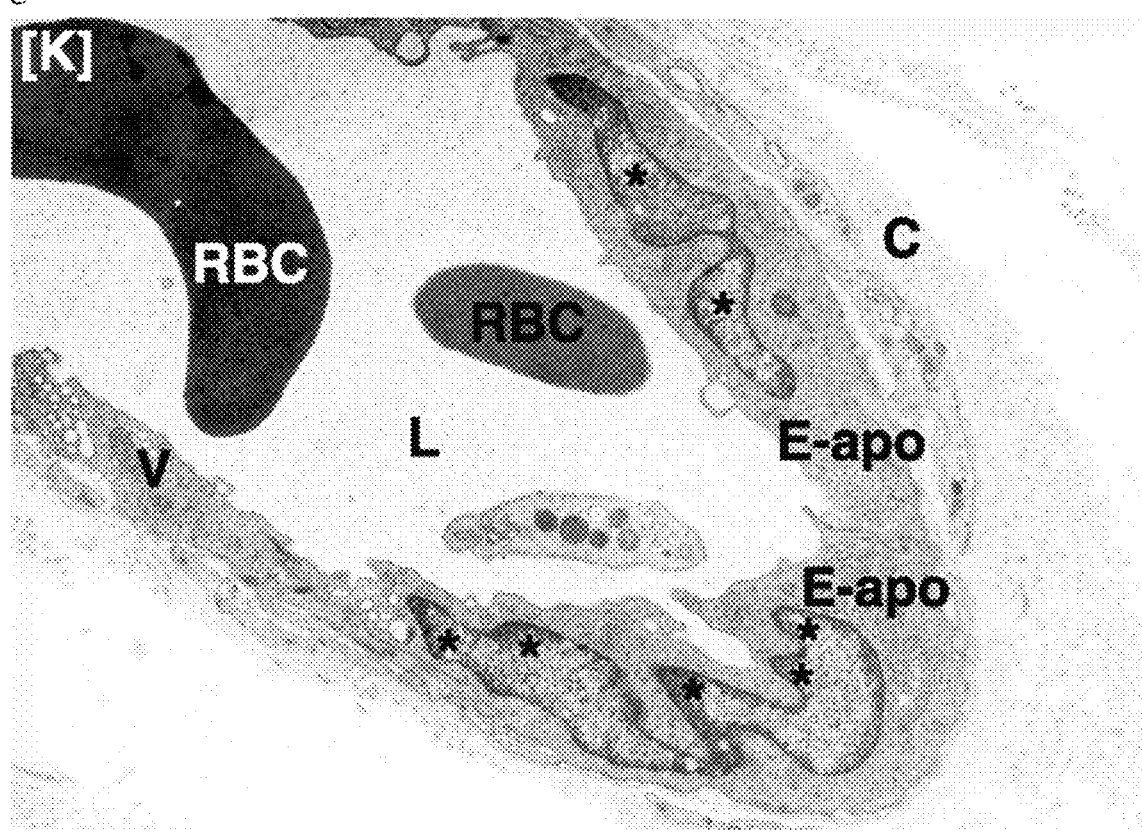
FIG. 11 is an electron micrograph of a tumor tissue of the tumor-bearing rat group with administration of zileuton (Example 4; dosing period, 3 days). RBC, red blood cell; L, intravascular lumen; V, blood vessel; C, collagen fiber; E-apo, apoptosis of vascular endothelial cell.
Figure 12:
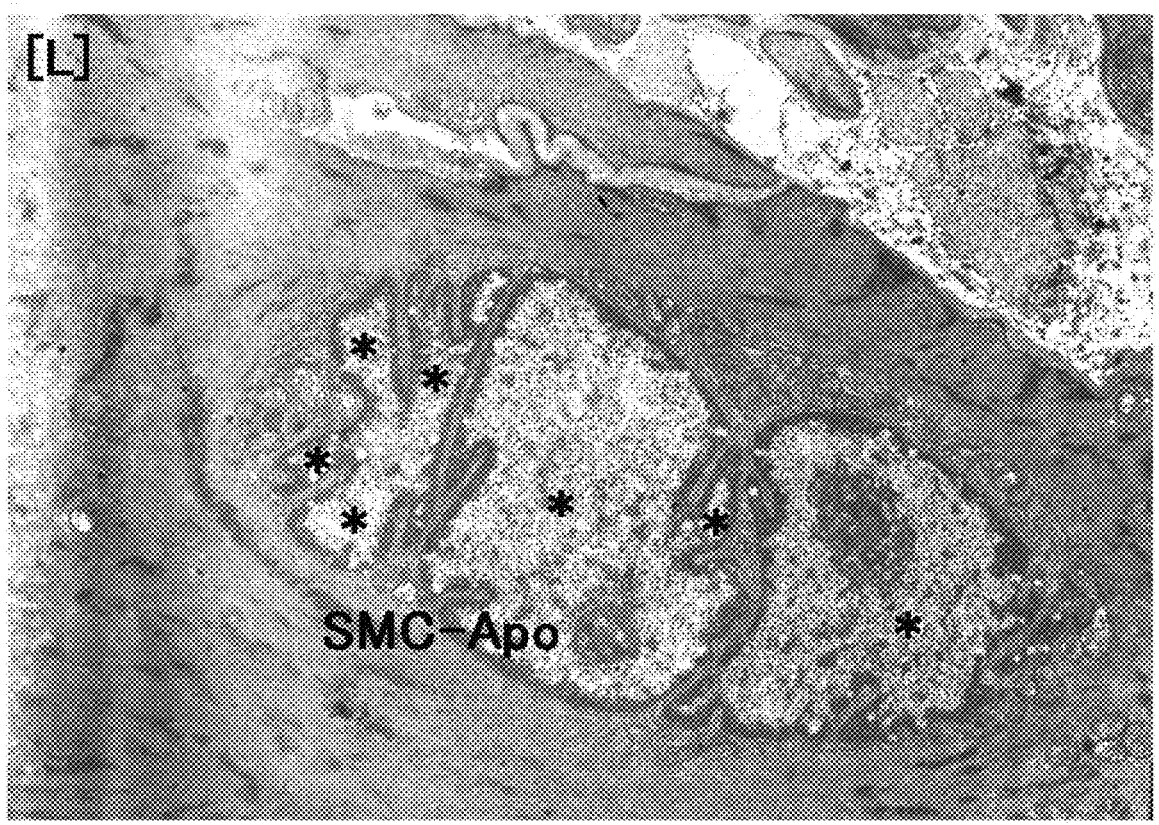
FIG. 12 is an electron micrograph of a smooth muscle cell in a tumor site of the tumor-bearing rat group with administration of montelukast sodium (Example 1; dosing period, 3 days). SMC-Apo, apoptosis of a smooth muscle cell.
Figure 13:
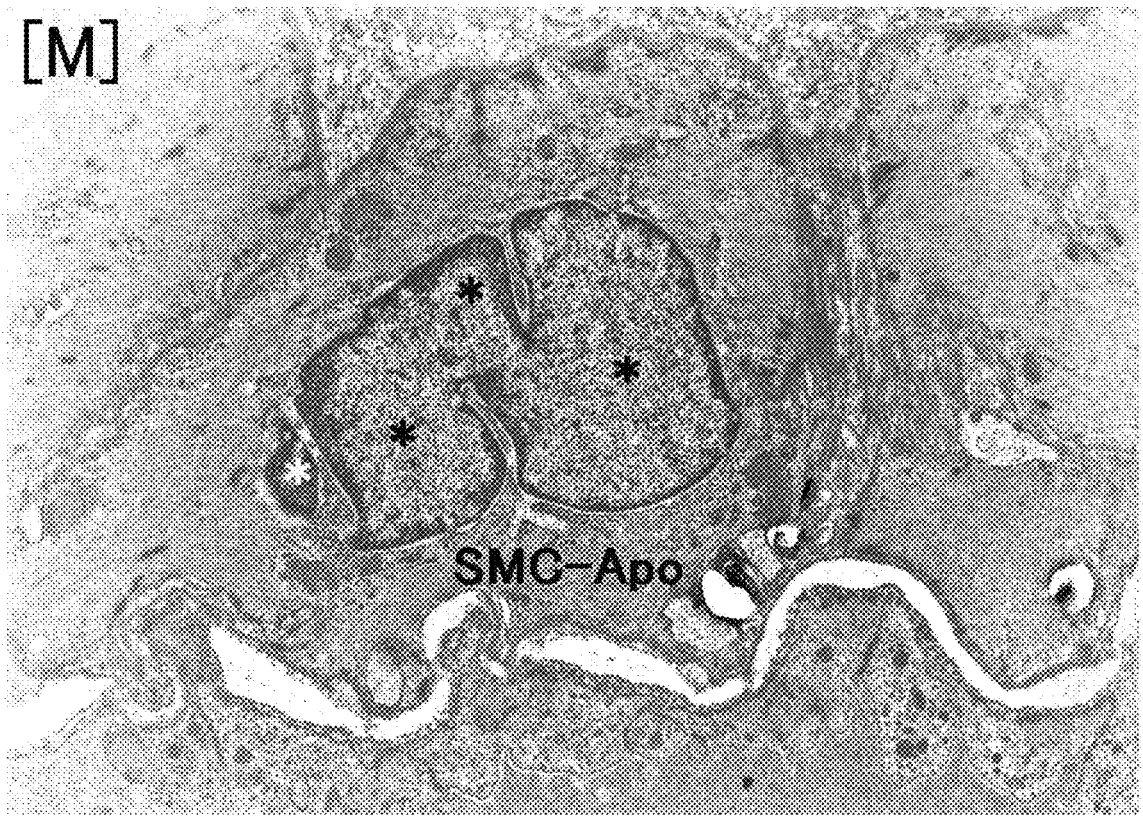
FIG. 13 is an electron micrograph of a smooth muscle cell in a tumor site of the tumor-bearing rat group with administration of pranlukast hydrate (Example 3; dosing period, 3 days). SMC-Apo, apoptosis of a smooth muscle cell.
Figure 14:
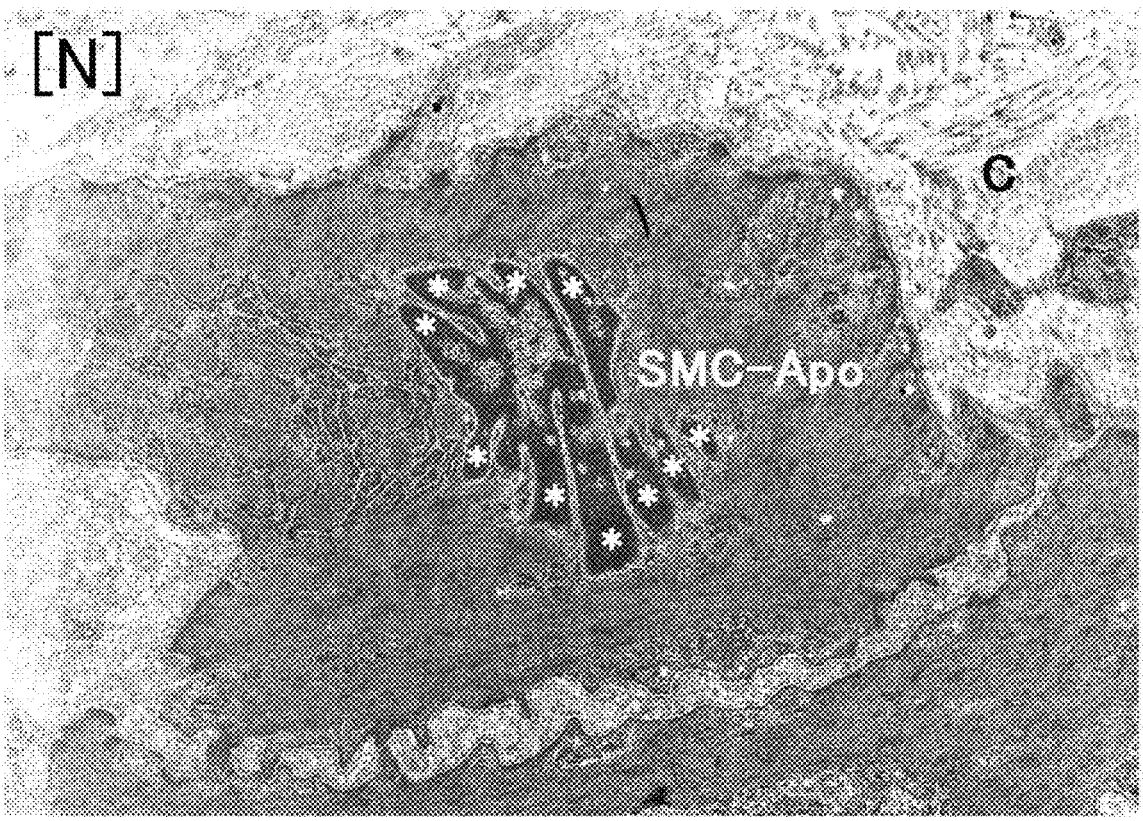
FIG. 14 is an electron micrograph of a smooth muscle cell in a tumor site of the tumor-bearing rat group with administration of zafirlukast (Example 2; dosing period, 3 days). SMC-Apo, apoptosis of a smooth muscle cell; C, collagen fiber.
Figure 15:
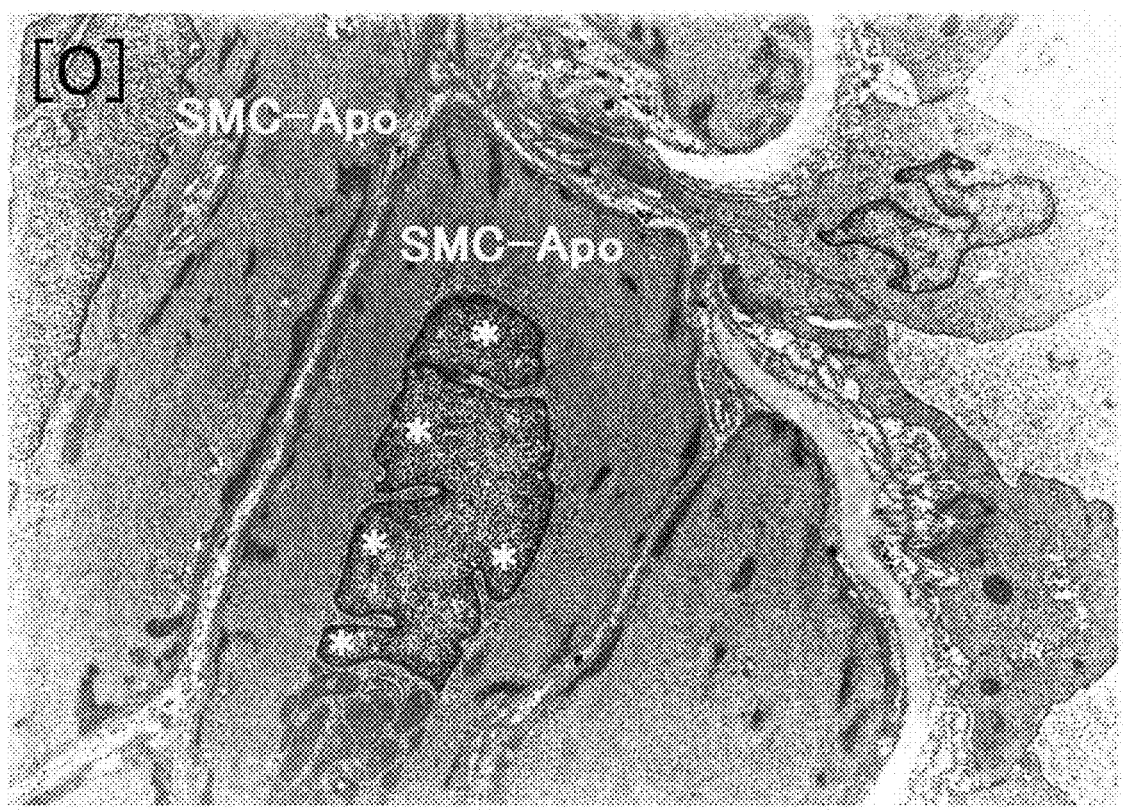
FIG. 15 is an electron micrograph of a smooth muscle cell in a tumor site of the tumor-bearing rat group with administration of zileuton (Example 4; dosing period, 3 days). SMC-Apo, apoptosis of a smooth muscle cell.
Figure 16:
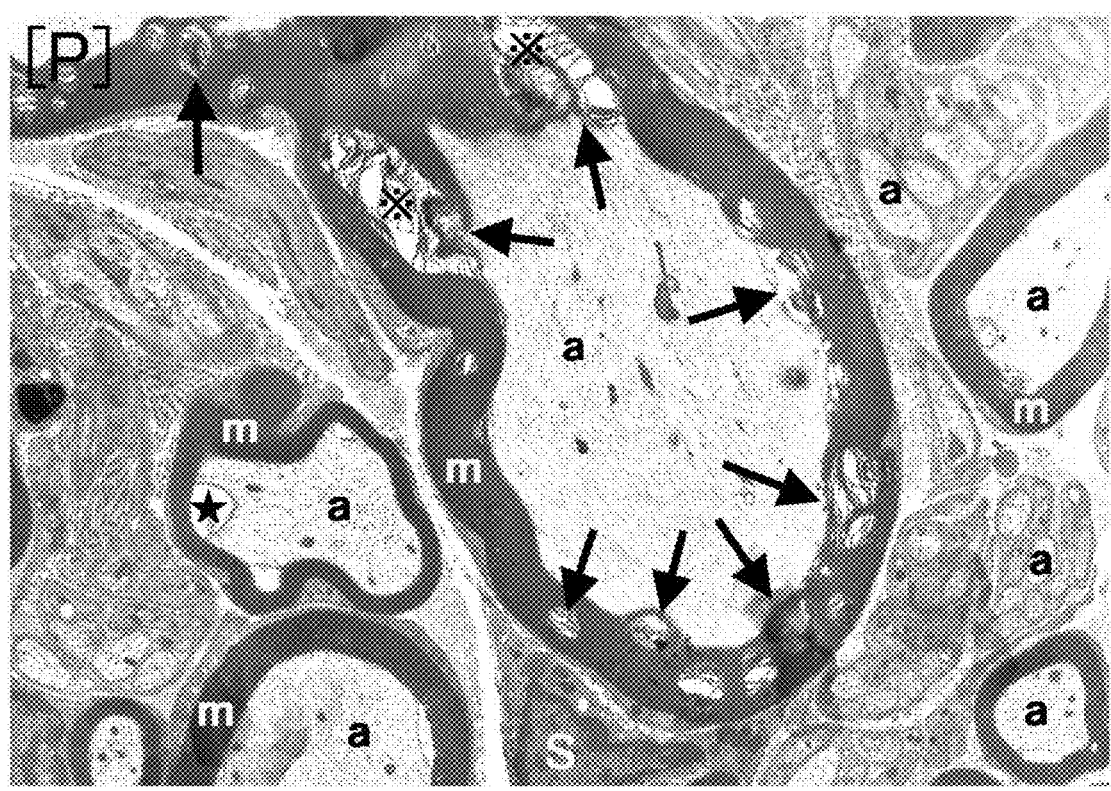
FIG. 16 is an electron micrograph of a peripheral nerve cell in a tumor site of the tumor-bearing rat group with administration of montelukast sodium (Example 1; dosing period, 3 days). a, axon; m, myelin sheath; ★, vacuolation and degeneration of an axon; arrow and ※, degeneration of a myelin sheath.
Figure 17:
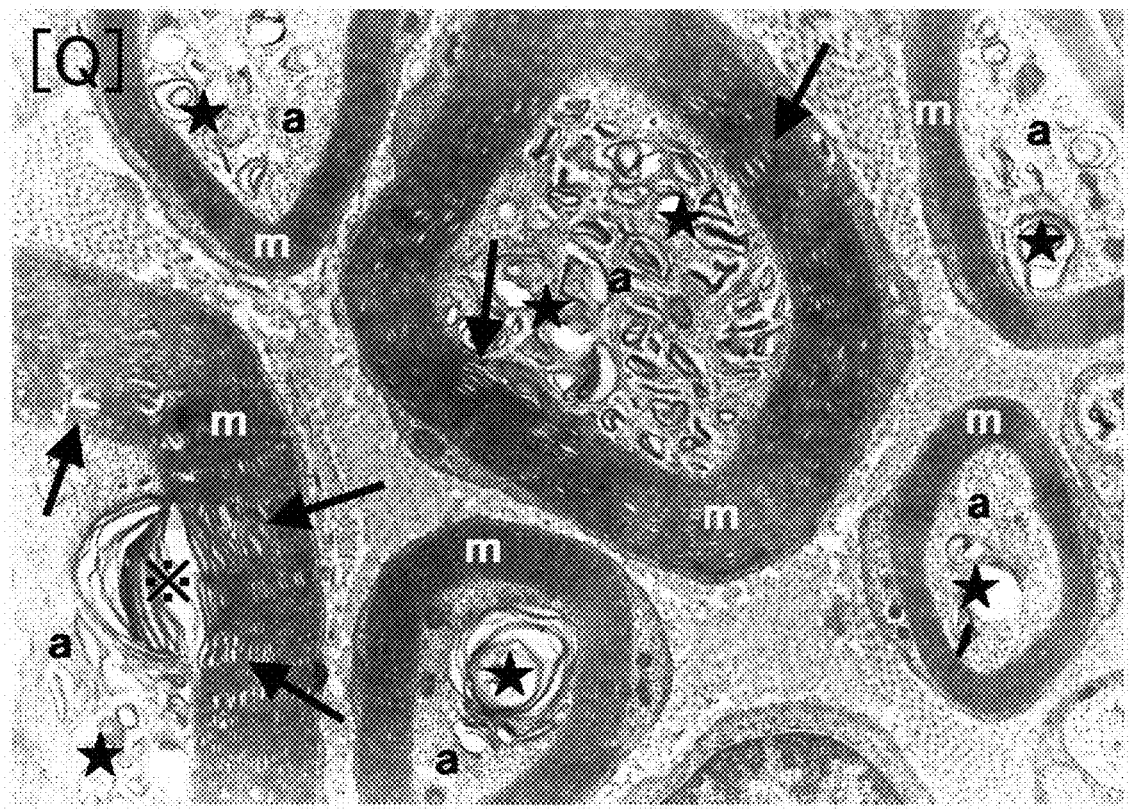
FIG. 17 is an electron micrograph of a peripheral nerve cell in a tumor site of the tumor-bearing rat group with administration of pranlukast hydrate (Example 3; dosing period, 3 days). a, axon; m, myelin sheath; ★, vacuolation and degeneration of an axon; arrow and ※, degeneration of a myelin sheath.
Figure 18:
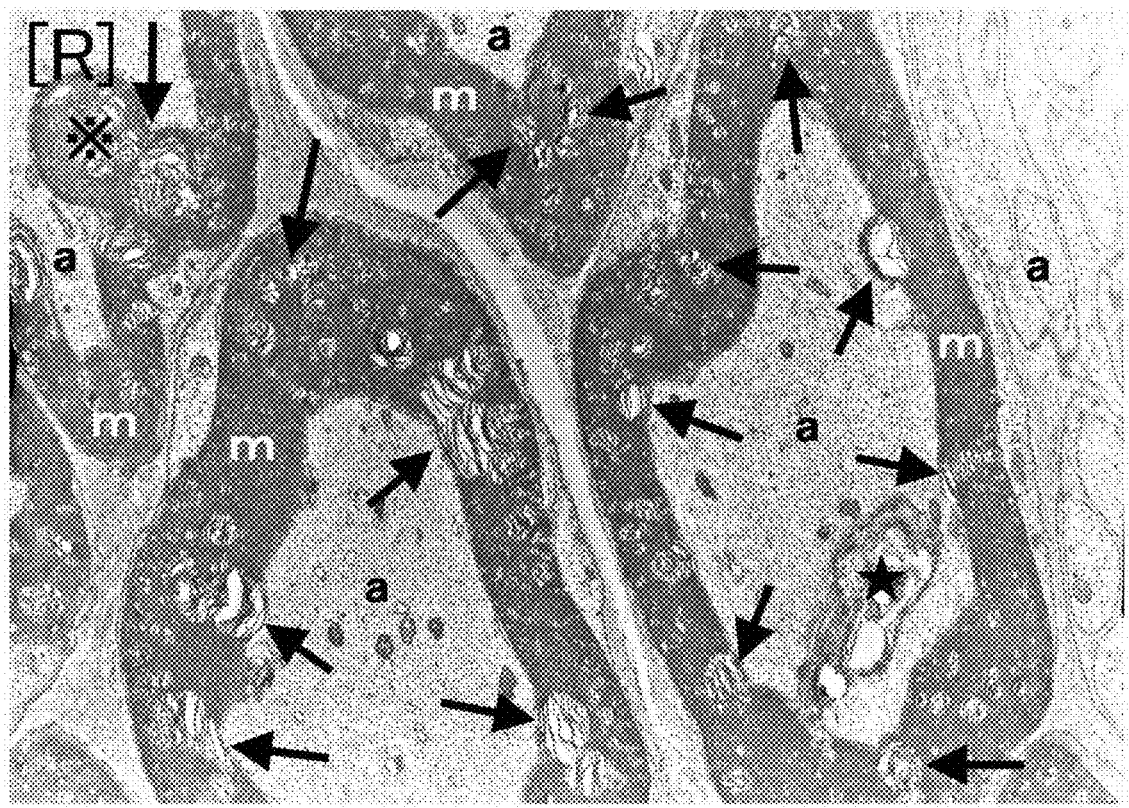
FIG. 18 is an electron micrograph of a peripheral nerve cell in a tumor site of the tumor-bearing rat group with administration of zafirlukast (Example 2; dosing period, 3 days). a, axon; m, myelin sheath; ★, vacuolation and degeneration of an axon; arrow and ※, degeneration of a myelin sheath.
Figure 19:
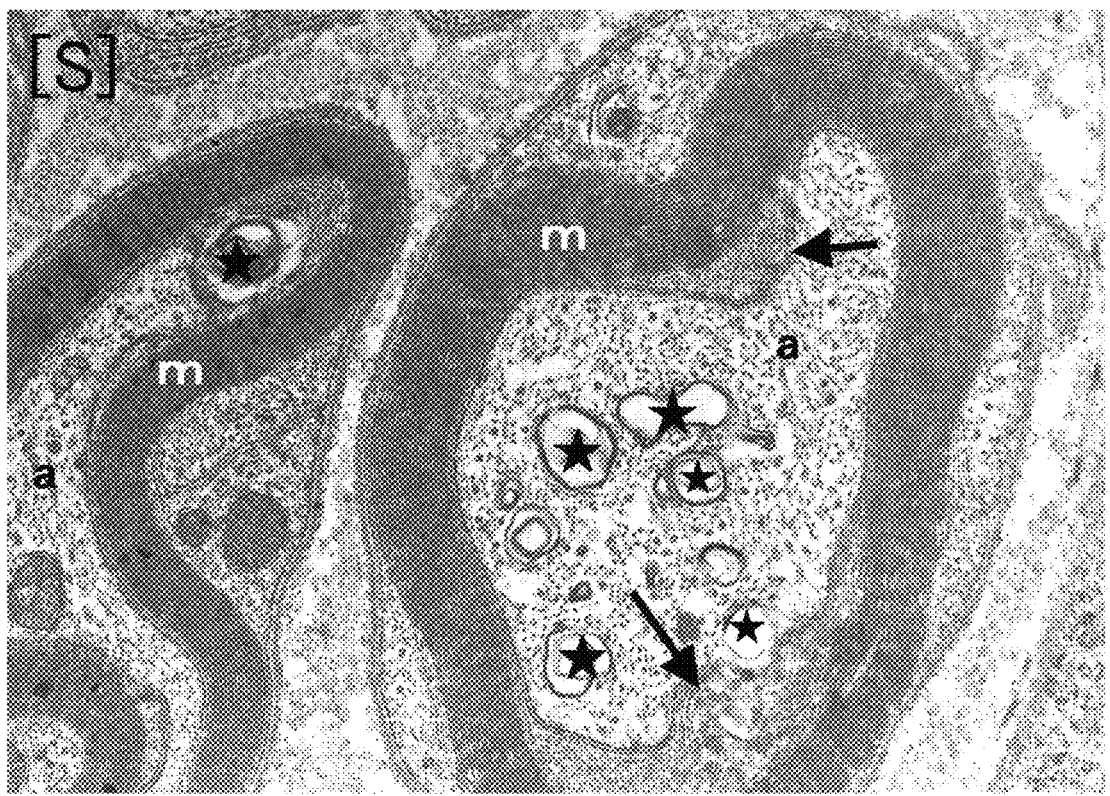
FIG. 19 is an electron micrograph of a peripheral nerve cell in a tumor site of the tumor-bearing rat group with administration of zileuton (Example 4; dosing period, 3 days). a, axon; m, myelin sheath; ★, vacuolation and degeneration of an axon; arrow, degeneration of a myelin sheath.
Figure 20:
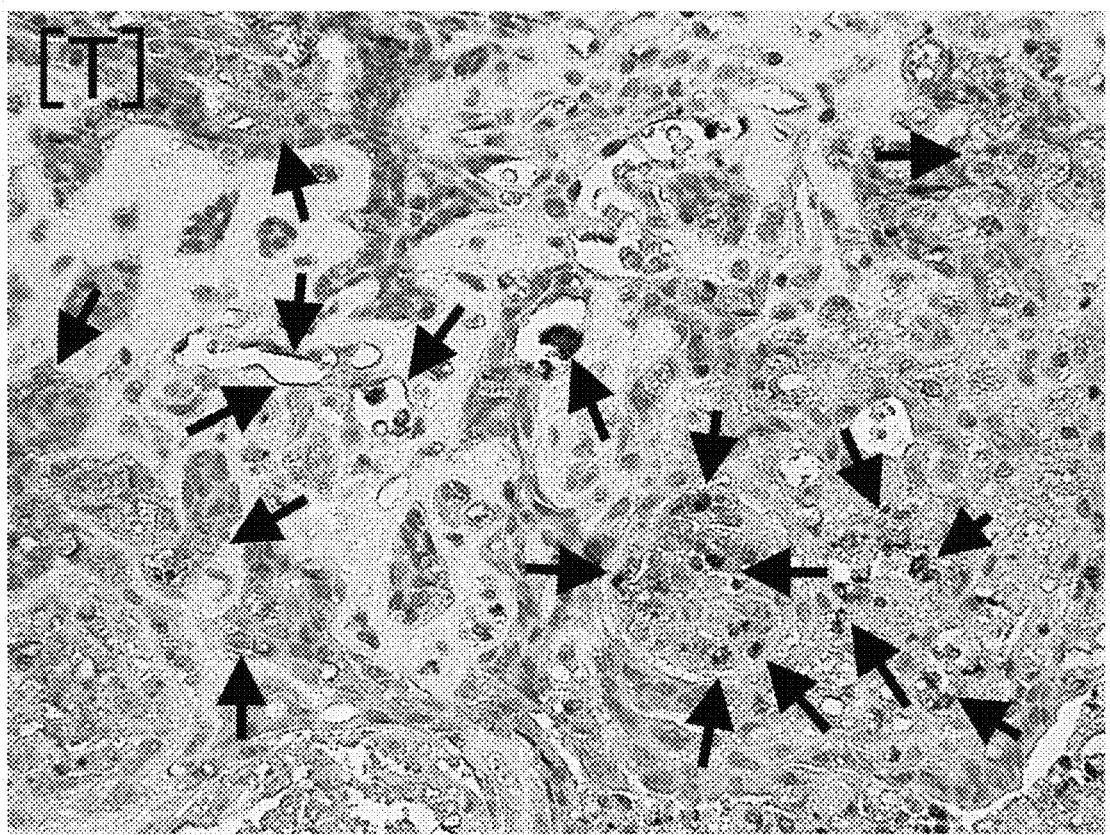
FIG. 20 is an immunostaining image of a spontaneously-developed rat mammary gland tumor tissue, which image was obtained with a leukotriene receptor antibody. Arrow, cell positively stained with the leukotriene receptor antibody (cell stained brown).
Figure 21:
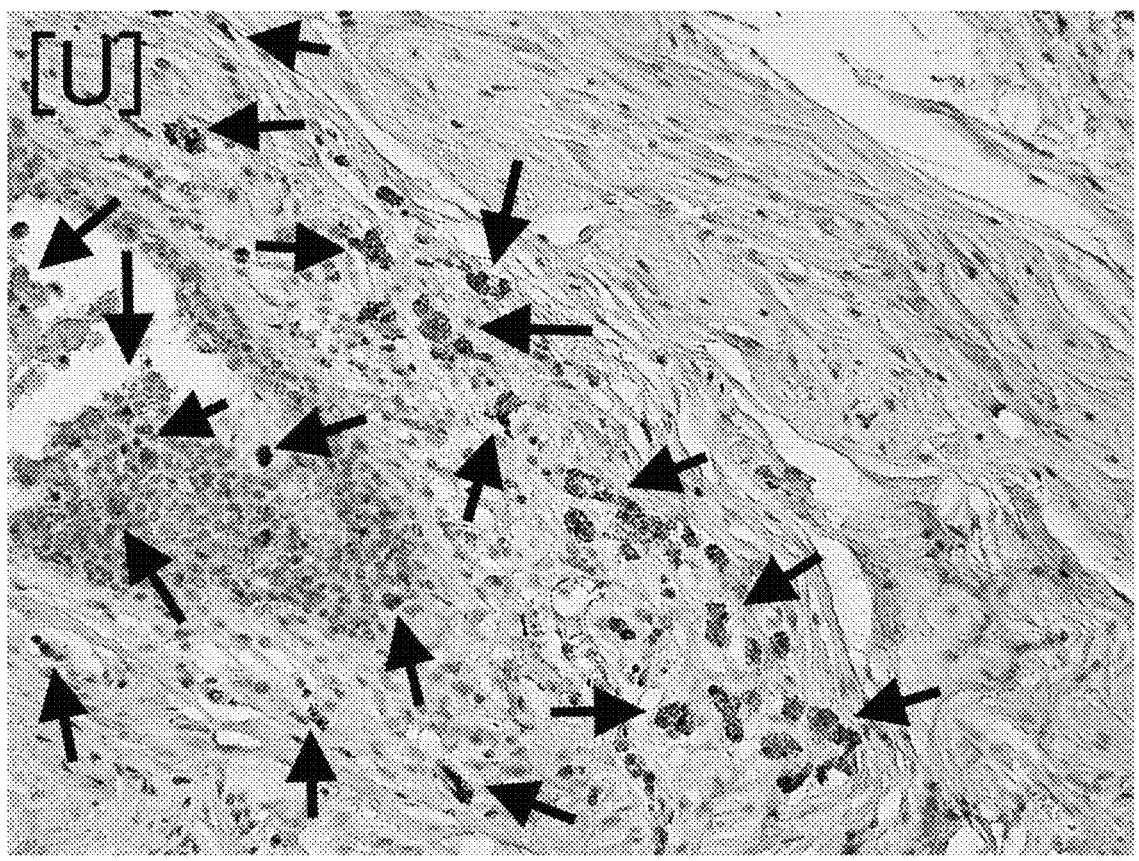
FIG. 21 is an immunostaining image of a human breast cancer tissue, which image was obtained with a leukotriene receptor antibody. Arrow, cell positively stained with the leukotriene receptor antibody (cell stained brown).
Figure 22:
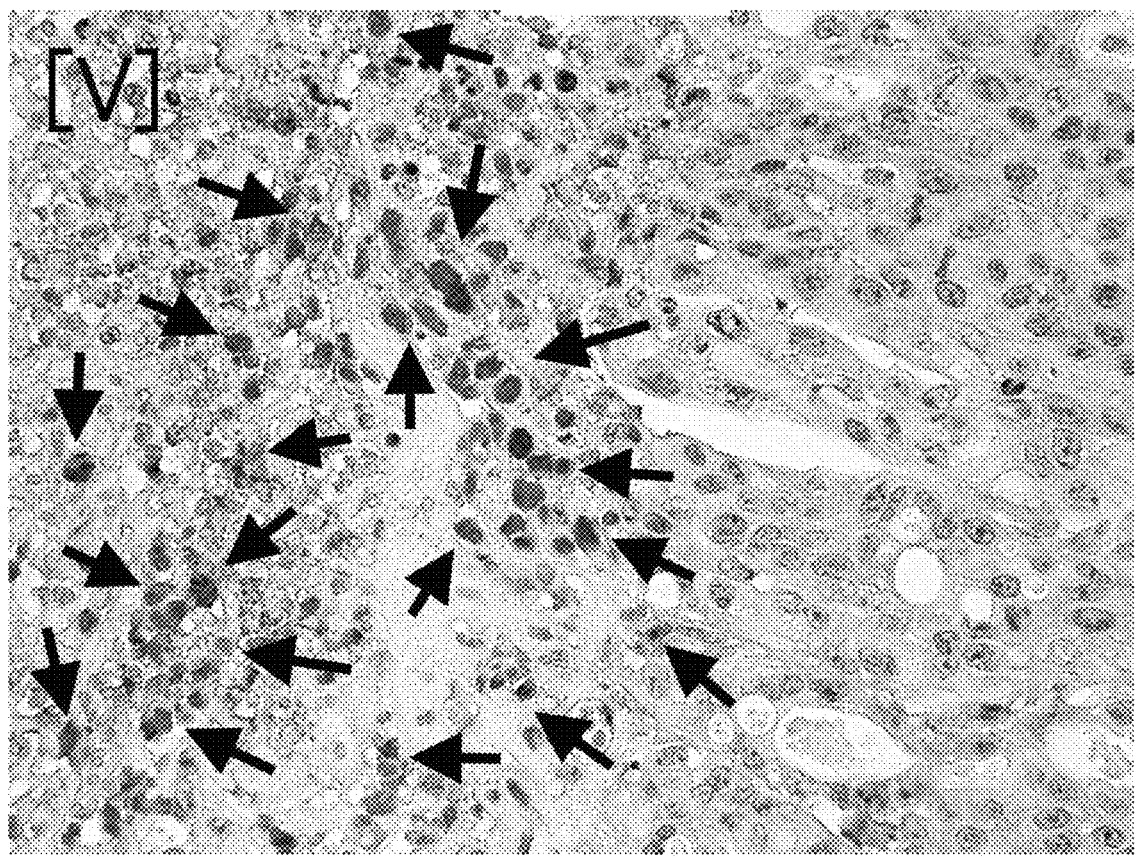
FIG. 22 is an immunostaining image of a human stomach cancer tissue, which image was obtained with a leukotriene receptor antibody. Arrow, cell positively stained with the leukotriene receptor antibody (cell stained brown).
Figure 23:
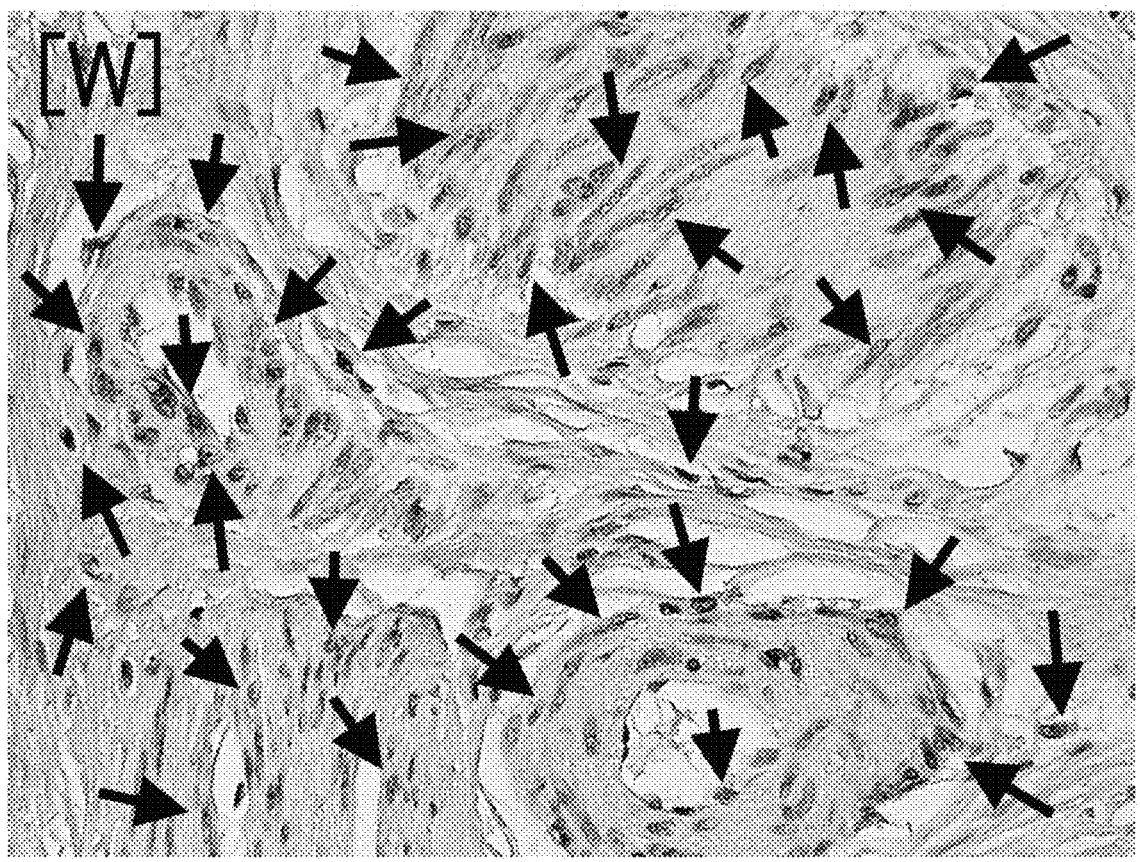
FIG. 23 is an immunostaining image of a human uterine leiomyoma, which image was obtained with a leukotriene receptor antibody. Arrow, cell positively stained with the leukotriene receptor antibody (cell stained brown).
Figure 24:
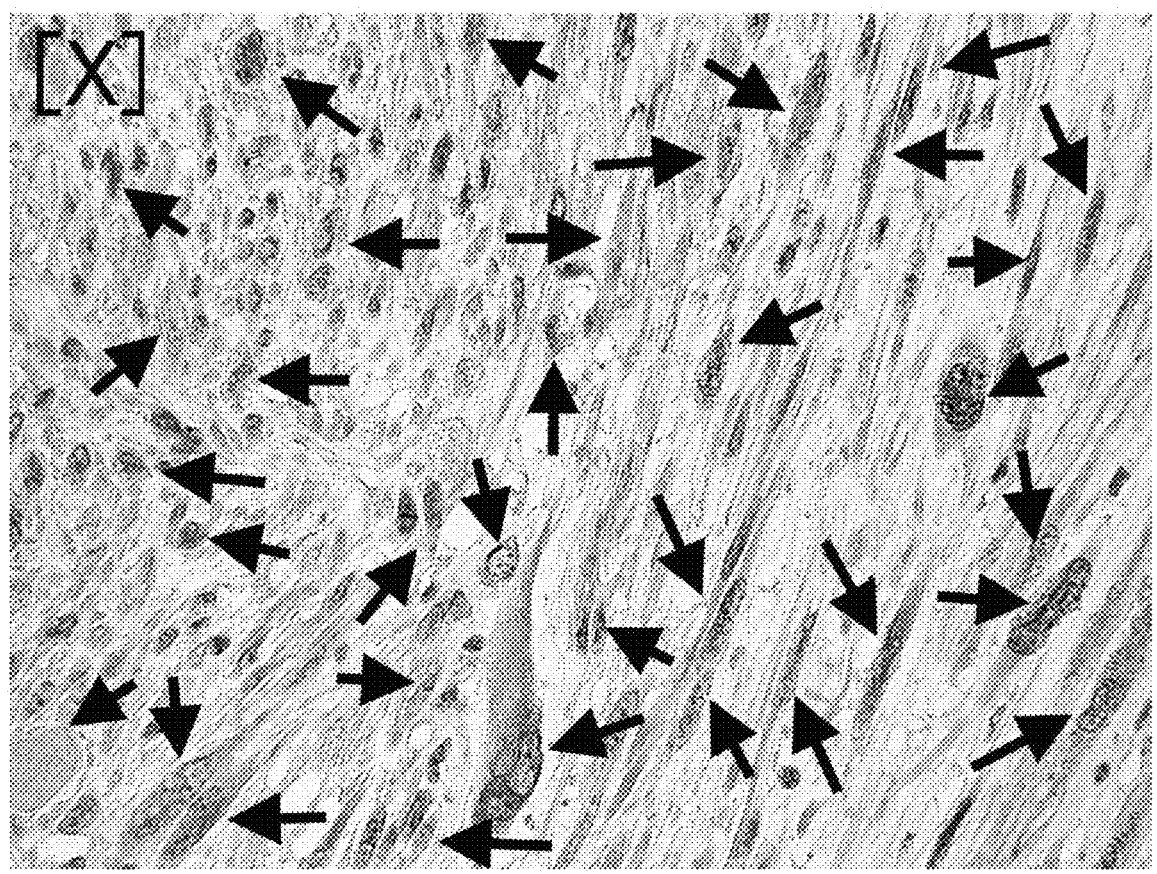
FIG. 24 is an immunostaining image of a human leiomyosarcoma, which image was obtained with a leukotriene receptor antibody. Arrow, cell positively stained with the leukotriene receptor antibody (cell stained brown).

FIGS. 10 and 11 are electron micrographs of tumor tissues of the group with administration of zileuton (Example 4, dosing period, 3 days). In blood vessels in the tumor tissues, apoptosis of endothelial cells (E-apo in the figures) was observed. These endothelial cells showed irregular condensation and fragmentation (* in the figures) of their nuclei. These conditions correspond to Stage II to III of apoptosis (T. Ihara, et al. 1998, described above). By the apoptosis of endothelial cells, an effect to inhibit blood flow into the tumor tissues (an inhibitory effect on newly formed blood vessels) could be obtained. Apoptosis of fibroblasts (F-apo in the figures), which produce collagen fibers and constitute the stroma of the tumor tissues, was also induced. Thus, an effect to inhibit stromal hyperplasia was also seen.

FIGS. 12 to 15 are electron micrographs of smooth muscle cells of the groups with administration of leukotriene inhibitors. In any of the treated groups, apoptosis of smooth muscle cells (SMC-Apo) in the tumor tissue was observed. These smooth muscle cells showed irregular condensation and fragmentation (*) of their groups. These conditions correspond to Stage II to III of apoptosis (T. Ihara, et al. 1998, described above). Due to the apoptosis of smooth muscle cells in the tumor tissues, an inhibitory effect on newly formed blood vessels (because apoptosis was also observed in smooth muscle cells in the vicinities of blood vessels) and an inhibitory effect on stromal hyperplasia (because smooth muscle cells, together with fibroblasts, produce collagen fibers, which are components constituting the stroma) were found. These findings were found only in the leukotriene inhibitor administration groups, and not found in the untreated group.

FIGS. 16 to 19 are electron micrographs of peripheral nerve cells of the groups with administration of leukotriene inhibitors. In peripheral nerves in the tumor tissues, degeneration of axons (a) and myelin sheaths (m) were observed. These findings indicate damage of the peripheral nerve cells. Thus, the administration of the leukotriene inhibitors produced an effect to suppress proliferation of nerves that extend side by side with blood vessels. In addition, an inhibitory effect on tumor pain can be obtained because of the suppression of nerve cell proliferation in the tumor tissue. These findings were found only in the leukotriene inhibitor administration groups, and not found in the untreated group. The degeneration was not observed at all in peripheral nerve cells in the contralateral side of the tumor site (non-tumor site) of each tumor-bearing rat in the groups with administration of leukotriene inhibitors. Therefore, the leukotriene inhibitors were thought to have no side effects.

Example 5: Investigation of Leukotriene Receptors by Immunostaining Using Leukotriene Receptor Antibody Whether leukotriene receptors are present or not was investigated for various tumor tissues using their paraffin sections, by an immunostaining method (Simple Stain MAX PO method, Nichirei Corporation) using leukotriene receptor antibodies (Polyclonal Antibody to CysLT1 and Polyclonal Antibody to CysLT2, Acris Antibodies GmbH). The tumor tissues investigated are shown in Table 1.

TABLE 1

| Rat | Spontaneous mammary gland tumor |
|---|---|
| Human | (Malignant tumors) stomach cancer, colon cancer, liver cancer, renal cancer, thyroid cancer, pharyngeal cancer, esophageal cancer, bile duct cancer, pancreatic cancer, breast cancer, prostate cancer, leiomyosarcoma, rhabdomyosarcoma, angiosarcoma (mammary gland) |
|  | (Benign tumors) pituitary adenoma, meningioma, goiter, neurilemmoma, leiomyoma |

In all tumor tissues investigated in the present Example, cells positive for the leukotriene receptor antibody could be found. Representative examples of the immunostaining images are shown in FIGS. 20 to 24.

The four kinds of leukotriene inhibitors used above are drugs which antagonistically act against leukotriene receptors or which inhibit production of leukotriene. Since a large number of leukotriene receptors are expressed in various cells in the tumor tissues, it is thought that the therapeutic effects against tumors are obtained by inhibition of signal transduction mediated by leukotriene receptors. Since expression of leukotriene receptors is observed in both epithelial and nonepithelial tumor tissues, leukotriene inhibitors are thought to exert their therapeutic effects in both tumor groups. Moreover, since expression of leukotriene receptors was also confirmed in benign tumor tissues, leukotriene inhibitors are thought to exert their therapeutic effects not only in malignant tumors, but also in benign tumors.

The invention claimed is:

1. A method for treatment of at least one malignant tumor in a subject in need thereof, said method comprising administering to said subject having at least one malignant tumor expressing leukotriene receptor an effective amount of at least one leukotriene inhibitor selected from the group consisting of: compounds selected from montelukast, zafirlukast, and pranlukast; pharmaceutically acceptable salts of said compounds; and pharmaceutically acceptable solvates of said compounds and said salts.

2. A method for treatment of a solid tumor(s) in a patient, comprising administering to the patient having a solid tumor(s) expressing leukotriene receptor an effective amount of at least one leukotriene inhibitor selected from the group consisting of: compounds selected from montelukast, zafirlukast, and pranlukast; pharmaceutically acceptable salts of said compounds; and pharmaceutically acceptable solvates of said compounds and said salts.

3. The method according to claim 1, wherein said at least one malignant tumor expressing leukotriene receptor is selected from leukotriene receptor-expressing malignant tumors excluding colon cancer and prostate cancer.

4. The method according to claim 1, wherein said at least one malignant tumor expressing leukotriene receptor is selected from stomach cancer, liver cancer, renal cancer, thyroid cancer, pharyngeal cancer, esophageal cancer, bile duct cancer, pancreatic cancer, breast cancer, leiomyosarcoma, rhabdomyosarcoma, and angiosarcoma (mammary gland).

5. The method according to claim 2, wherein said solid tumor(s) expressing leukotriene receptor is selected from leukotriene receptor-expressing solid tumors excluding colon cancer and prostate cancer.

6. The method according to claim 2, wherein said solid tumor(s) expressing leukotriene receptor is selected from stomach cancer, liver cancer, renal cancer, thyroid cancer, pharyngeal cancer, esophageal cancer, bile duct cancer, pancreatic cancer, breast cancer, leiomyosarcoma, rhabdomyosarcoma, angiosarcoma (mammary gland), pituitary adenoma, meningioma, goiter, neurilemmoma, and leiomyoma.

\* \* \* \* \*